(12) United States Patent
Majeti et al.

(10) Patent No.: US 11,504,339 B2
(45) Date of Patent: Nov. 22, 2022

(54) COMPOSITIONS COMPRISING UROLITHIN A AND USES THEREOF IN TREATING KIDNEY INJURY

(71) Applicant: THE TEXAS A&M UNIVERSITY SYSTEM, College Station, TX (US)

(72) Inventors: Naga Venkata Ravi Kumar Majeti, College Station, TX (US); Raghu Ganugula, College Station, TX (US); Meenakshi Arora, College Station, TX (US); Dianxiong Zou, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 17/160,836

(22) Filed: Jan. 28, 2021

(65) Prior Publication Data

US 2021/0236434 A1 Aug. 5, 2021

Related U.S. Application Data

(60) Provisional application No. 62/967,908, filed on Jan. 30, 2020.

(51) Int. Cl.
| | | |
|---|---|---|
| *A61K 9/51* | (2006.01) | |
| *A61K 31/282* | (2006.01) | |
| *A61K 47/69* | (2017.01) | |

(52) U.S. Cl.
CPC ............ *A61K 9/513* (2013.01); *A61K 31/282* (2013.01); *A61K 9/5123* (2013.01); *A61K 9/5153* (2013.01); *A61K 47/6929* (2017.08)

(58) Field of Classification Search
CPC . A61K 47/6929; A61K 9/5123; A61K 9/5153
See application file for complete search history.

(56) References Cited

U.S. PATENT DOCUMENTS

| 2018/0110865 A1 | 4/2018 | Majeti et al. |
| 2018/0214386 A1 | 8/2018 | Majeti et al. |

OTHER PUBLICATIONS

Zou et al. "Oral delivery of nanoparticle urolithin A normalizes cellular stress and improves survival in mouse model of cisplatin-induced AKI", Am J Physiol Renal Physiol 317: F1255-F1264, 2019 (Year: 2019).*

Guada et al. "Urolithin A Mitigates Cisplatin-Induced Nephrotoxicity by Inhibiting Renal Inflammation and Apoptosis in an Experimental Rat Model", J Pharmacol Exp Ther 363:58-65, Oct. 2017 (Year: 2017).*

Saini et al. "The Next Generation Noncompetitive Active Polyester Nanosystems for Transferrin Receptor-mediated Peroral Transport Utilizing Gambogic Acid as a Ligand", Sci. Rep. 6, 29501, 2016 (Year: 2016) (Year: 2016).*

Zou, D. et al., "Oral delivery of nanoparticle urolithin A normalizes cellular stress and improves survival in mouse mode of cisplatin-induced AKI," 2019, American Journal of Physiology-Renal Physiology, 317(5), p. F1255-F1264.

* cited by examiner

*Primary Examiner* — James W Rogers
(74) *Attorney, Agent, or Firm* — Barnes & Thornburg LLP

(57) ABSTRACT

The present disclosure provides nanoparticle compositions comprising i) a polymeric nanoparticle, ii) one or more ligands conjugated to the polymeric nanoparticle, and iii) urolithin A. The disclosure also provides methods and pharmaceutical compositions comprising the nanoparticle compositions for use in treating patients with various disease states.

10 Claims, 11 Drawing Sheets

Specification includes a Sequence Listing.

COMPOSITIONS COMPRISING UROLITHIN A AND USES THEREOF IN TREATING KIDNEY INJURY

CROSS-REFERENCE TO RELATED APPLICATIONS

This application claims the benefit under 35 USC § 119(e) of U.S. Provisional Application Ser. No. 62/967,908, filed on Jan. 30, 2020, the entire disclosure of which is incorporated herein by reference.

BACKGROUND AND SUMMARY OF THE INVENTION

Urolithin A (UA) is the gut-microbial metabolite of ellagic acid, a polyphenol known to have antioxidant and anti-inflammatory properties. In particular, UA has been reported to have superior benefits over its precursor ellagic acid for the reduction of plasma cytokines and the inhibition of intracellular inflammatory as well as for apoptotic signaling. Thus, UA may offer therapeutic benefits to certain patient populations.

However, administration of UA to patients is problematic due to its poor absorption in the gastrointestinal (GI) tract. Furthermore, the poor oral bioavailability of UA results in the requirement for frequent dosing to patients, as well as the necessity for high doses to be given to patients. Therefore, there exists a need for compositions and methods that are efficacious in delivering UA to patients for therapeutic uses.

Accordingly, the present disclosure provides nanoparticle compositions comprising UA that can formulated for improved delivery to patients, including oral administration. Furthermore, the present disclosure provides several methods of administering the nanoparticle compositions to patients in various disease states for which UA can be therapeutically beneficial.

The compositions and methods of the present disclosure provide several advantages compared to the current state of the art. First, the nanoparticle compositions are capable of being formulated for oral administration for improved delivery of UA to patients. Furthermore, the nanoparticle compositions can be utilized in methods of treating patients with kidney injury, for example acute kidney injury (AKI). There are currently no FDA-approved drugs for treating AKI in patients even though this disease is a common and serious manifestation that causes approximately 1.7 million deaths each year.

Finally, the nanoparticle compositions can be utilized in methods of treating other disease states for which UA may be therapeutically beneficial. The methods include treatment of patients with lupus, inflammatory disorders, and diseases associated with aging.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1A shows DLS measurement of nanoparticle size and polydispersity index (PDI), with an inset showing pH and ζ-potential (mean±SEM). FIG. 1B shows scanning electron photomicrograph of P2Ns-GA nanoparticles with UA (bar 1 µm). FIG. 1C shows data from healthy male Sprague-Dawley rats given a single dose of plain or UA-containing nanoparticle compositions (50, 25 or 10 mg/kg per animal) by oral gavage, noted as "P2Ns-GA UA". Plasma UA concentrations were determined by LC-MS at various time points 0.5-48 hours post-dosing. FIG. 1D shows a summary of area under curve (AUC), $T_{max}$ (time to achieve $C_{max}$), and $C_{max}$ (peak concentration) of the four groups.

FIG. 2A shows a survival plot of male C57BL/6J mice in CIS only (CIS control), CIS with treatment (P2Ns-GA UA nanoparticle compositions), and negative control (Neg control) groups. (n=4-8 per group). FIG. 2B shows a weight loss plot of CIS control and P2Ns-GA UA groups, as compared to initial animal weight prior to CIS injection. (n=4 per group). FIG. 2C shows a ratio of kidney mass to body weight at sacrifice. (n=4 per group). FIG. 2D shows blood urea nitrogen (BUN) and serum creatinine levels at sacrifice (n=4 per group). All data expressed as mean±SEM, and analyzed using unpaired Student's t test between two groups or ANOVA among multiple groups followed by Tukey post-test. *P<0.05; P<0.01; *P<0.001 versus CIS control group.

FIG. 3A shows representative H&E micrographs of each group (n=4) showing the kidneys at study termination. Original 4× magnified images (left) and images digitally magnified to the boxed areas (right) are shown side by side. The CIS control group showed marked tubular injury as evidenced by increased necrosis and atrophy as well as expansion of interstitial space. Boxed areas indicate magnified renal tubules. (Bar 200 µm for original and bar 50 µm for zoomed images). FIG. 3B shows representative Periodic acid-Schiff (PAS) stained micrographs of each group (n=4) showing kidney injury and apoptosis in the CIS control group at study termination. Asterisks indicate detached cells in dilated tubules (top left panel) and Tamm Horsfall protein-containing renal casts (bottom left panel). Diameters of glomeruli also appeared enlarged in the CIS control group, along with thickening of the basement membrane. Darker color represents PAS-positive staining. Original magnification 40×, (bar 50 µm). FIG. 3C shows quantification of interstitial expansion (i.e. % area occupied by interstitial space) observed for each group (n=4 per group). FIG. 3D shows quantification of glomerular diameter observed under 40×PAS staining for each group (n=30 per group). All data expressed as mean±SEM, and analyzed using ANOVA between multiple groups followed by Tukey post-test. ****P<0.0001 versus CIS control group. #P<0.05 versus Neg control group.

FIG. 4A shows differential expression of mature miRs: miR-192-5p and miR-140-5p, normalized to the U6 snRNA (n=4 per group). FIG. 4B shows Western blots of NRF2, P53, and GAPDH. FIG. 4C shows expression of NRF2-inducible genes: Mt1, Txnrd1, and Srxn1, normalized to β-actin (n=4 per group). FIG. 4D shows expression of P53-inducible genes: Cdkn1a, Atf3, and Trp53inp1, normalized to β-actin (n=4 per group). FIG. 4E shows expression of β-catenin and Tcf7, normalized to β-actin (n=4 per group). FIG. 4F shows expression of HIF1α and Pgk1, normalized to β-actin (n=4 per group). All data are expressed as mean±SEM and analyzed using ANOVA between multiple groups followed by Tukey post-test. *P<0.05; P<0.01; *P<0.001; ****P<0.0001 versus CIS control. #P<0.05; ##P<0.01; ####P<0.0001 versus Neg control.

FIG. 5A shows expression of PARP1 and PARG, normalized to β-actin in all three experimental groups (n=4 per group). FIG. 5B shows expression of Bcl2 and Bax, normalized to β-actin in all three experimental groups (n=4 per group). FIG. 5C shows a summary of Bcl-2/Bax mRNA ratios and intracellular NAD concentration, normalized to total protein (n=4 per group). FIG. 5D shows a Western blot of mitochondrial OXPHOS complexes I-V along with GAPDH in all three experimental groups. FIG. 5E shows apoptotic cells (bright points) in the renal cortex and medulla were detected by the TUNEL assay, while nuclei were counterstained with DAPI (blue) at 20× original magnification (bar 100 μm). TUNEL-positive cells were quantified by ImageJ software (n=4 per group). All data expressed as mean±SEM, and analyzed using unpaired Student's t test between two groups or ANOVA between multiple groups followed by Tukey post-test. P<0.01; **P<0.0001 versus CIS control group (ANOVA). #P<0.05; ##P<0.01; ###P<0.001 versus CIS control (Student's t test). NS not statistically significant versus CIS control.

DETAILED DESCRIPTION

Figures 1A, 1B, 1C, 1D:
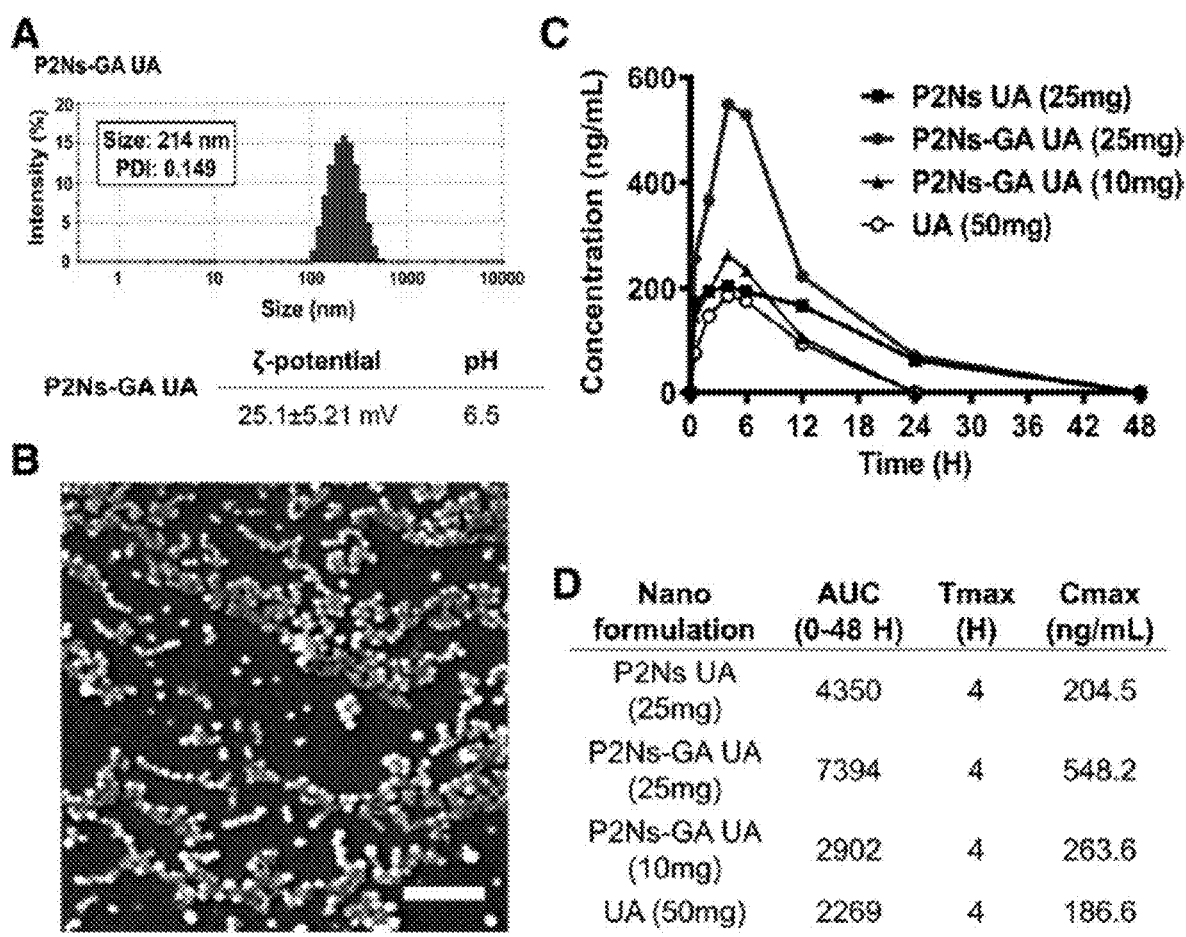
FIGS. 1A-1D show nanoparticle formulation and bioavailability.

Various embodiments of the invention are described herein as follows. In an illustrative aspect, a nanoparticle composition is provided. The nanoparticle composition comprises i) a polymeric nanoparticle, ii) one or more ligands conjugated to the polymeric nanoparticle, and iii) urolithin A.

Urolithin A, also known by its IUPAC name 3,8-Dihydroxybenzo[c]chromen-6-one, is a compound in the class of organic compounds known as benzo-coumarins or dibenzo-α-pyrones. The chemical structure of urolithin A is:

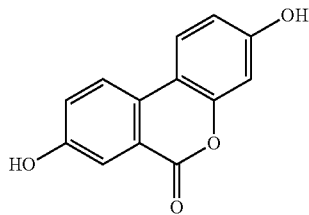 [SMILES: O=c1oc2cc(O)ccc2c2ccc(O)cc12]

As used herein, the term "urolithin A" refers to urolithin A base, pharmaceutically acceptable salts of urolithin A, other salts of urolithin A, and metabolites of urolithin A. The term "pharmaceutically acceptable salt" refers to an addition salt that exists in conjunction with the acidic or basic portion of urolithin A. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when urolithin A and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when urolithin A and any of its intermediates containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the present invention. They may serve as intermediates in the purification of compounds or in the preparation of other pharmaceutically-acceptable salts, or are useful for identification, characterization or purification.

In an embodiment, the polymeric nanoparticle comprises a polymer/copolymer selected from the group consisting of polylactide, poly(lactide-co-glycolide), polycaprolactone, and any combination thereof. In an embodiment, the urolithin A is encapsulated by the polymeric nanoparticle.

In an embodiment, the ligand is gambogic acid. It is well known in the art that gambogic acid (GA) is a noncompetitive ligand of the transferrin receptor (TfR1). Without being bound by any theory, it is believed that conjugation of GA to polymeric nanoparticles can facilitate transfer of the polymeric nanoparticles through the gastrointestinal barrier via TFRC (Transferrin Receptor 1) interaction. Furthermore, GA binding does not appear to interfere with normal transferrin-mediated iron metabolism to advantageously provide intestinal transport of the polymeric nanoparticles. Moreover, without being bound by any theory, it is also believed that conjugation of GA to polymeric nanoparticles can facilitate transfer of the polymeric nanoparticles across the blood-brain barrier (BBB).

The term "nanoparticle" refers to a particle having a size measured on the nanometer scale. As used herein, the "nanoparticle" refers to a particle having a structure with a size of less than about 1,000 nanometers. As used herein, the term "nanoparticle composition" refers to any substance that contains at least one nanoparticle. In some embodiments, a nanoparticle composition is a uniform collection of nanoparticles.

Methods for formulation of nanoparticle compositions using polymer/copolymer and/or GA can be found, for example, in U.S. Patent Application Publication No. 2018/0110865 and U.S. Patent Application Publication No. 2018/0214386, both herein incorporated by reference in their entireties.

In an embodiment, the nanoparticle composition has an average diameter from about 0.5 nm to about 1000 nm. Particle sizes are determined by methods well known in the art, such as by dynamic light scattering, SEM. In an embodiment, the nanoparticle composition has an average diameter from about 1 nm to about 500 nm. In an embodiment, the nanoparticle composition has an average diameter from about 10 nm to about 400 nm. In an embodiment, the nanoparticle composition has an average diameter from about 100 nm to about 400 nm. In an embodiment, the nanoparticle composition has an average diameter from about 100 nm to about 300 nm. In an embodiment, the nanoparticle composition has an average diameter from about 100 nm to about 200 nm. In an embodiment, the nanoparticle composition has an average diameter from about 100 nm to about 150 nm. In an embodiment, the nanoparticle composition has an average diameter from about 200 nm to about 400 nm. In an embodiment, the nanoparticle composition has an average diameter from about 300 nm to about 400 nm. In an embodiment, the nanoparticle composition has an average diameter from about 150 nm to about 300 nm. In an embodiment, the nanoparticle composition has an average diameter from about 150 nm to about 200 nm. In an embodiment, the nanoparticle composition has an average diameter from about 200 nm to about 300 nm. In an embodiment, the nanoparticle composition has an average diameter from about 250 nm to about 300 nm.

In an embodiment, the nanoparticle composition is lyophilized.

In an illustrative aspect, a pharmaceutical composition is provided. The pharmaceutical composition comprises a nanoparticle composition, wherein the nanoparticle composition comprises i) a polymeric nanoparticle, ii) one or more ligands conjugated to the polymeric nanoparticle, and iii) urolithin A.

The previously described embodiments of the nanoparticle composition are also applicable to the pharmaceutical composition.

In an embodiment, the pharmaceutical composition is an oral formulation. In an embodiment, the oral formulation is selected from the group consisting of a tablet, a capsule, a suspension, an emulsion, a syrup, a colloidal dispersion, a dispersion, and an effervescent composition.

In an embodiment, the pharmaceutical composition is a parenteral formulation. In an embodiment, the parenteral formulation is selected from the group consisting of intravenous, intraarterial, intraperitoneal, intrathecal, intradermal, epidural, intracerebroventricular, intraurethral, intrasternal, intracranial, intratumoral, intramuscular and subcutaneous.

In an embodiment, the pharmaceutical composition comprises one or more pharmaceutically acceptable carriers. Such pharmaceutically acceptable carriers include those listed in HANDBOOK OF PHARMACEUTICAL EXCIPIENTS, P. J. Sheskey et al. (Eds.), Pharmaceutical Press, 2017 which are known to the skilled artisan.

In an embodiment, the pharmaceutical composition further comprises a second therapeutic agent. In some aspects, the pharmaceutical composition is adapted for administration with a second therapeutic agent. The second therapeutic agent can comprise a compound disclosed herein or a compound, pharmaceutical, or other chemical entity that is shown to be therapeutically effective in treating or affecting one or more disease state of the present disclosure.

In an embodiment, the pharmaceutical composition is formulated as a single dose. In an embodiment, the pharmaceutical composition is a single unit dose. As used herein, the term "unit dose" is a discrete amount of the composition comprising a predetermined amount of the compound. The amount of the compound is generally equal to a dosage which would be administered to an animal or a convenient fraction of such a dosage such as, for example, one-half or one-third of such a dosage.

In an illustrative aspect, a method of treating a kidney injury in a patient in need thereof is provided. The method comprises the step of administering a therapeutically effective amount of a nanoparticle composition to the patient, wherein the nanoparticle composition comprises i) a polymeric nanoparticle, ii) one or more ligands conjugated to the polymeric nanoparticle, and iii) urolithin A.

The previously described embodiments of the nanoparticle composition and the pharmaceutical composition are also applicable to the method of treating a kidney injury. In an embodiment, the kidney injury is an acute kidney injury. In an embodiment, the kidney injury is a chronic kidney injury. In an embodiment, the kidney injury is a drug-induced kidney injury.

In an embodiment, the kidney injury is an anticancer drug-induced kidney injury. In an embodiment, the anticancer drug is a platinum-based antineoplastic. In an embodiment, the anticancer drug is cisplatin. In an embodiment, the anticancer drug is carboplatin. In an embodiment, the anticancer drug is oxaliplatin. In an embodiment, the anticancer drug is nedaplatin. In an embodiment, the patient is an animal. In an embodiment, the animal is a mammal. In an embodiment, the animal is a human.

In an embodiment, the nanoparticle composition is administered to the patient at a dose of about 0.001 to about 1000 mg of the nanoparticle composition per kg of body weight. In an embodiment, the nanoparticle composition is administered to the patient at a dose of about 0.001 to about 100 mg of the nanoparticle composition per kg of body weight. In an embodiment, the nanoparticle composition is administered to the patient at a dose of about 0.001 to about 10 mg of the nanoparticle composition per kg of body weight. In an embodiment, the nanoparticle composition is administered to the patient at a dose of about 1 to about 5 mg of the nanoparticle composition per kg of body weight.

In an embodiment, the nanoparticle composition is administered to the patient at a dose of about 100 mg of urolithin A. In an embodiment, the nanoparticle composition is administered to the patient at a dose of about 250 mg of urolithin A. In an embodiment, the nanoparticle composition is administered to the patient at a dose of about 500 mg of urolithin A. In an embodiment, the nanoparticle composition is administered to the patient at a dose of about 750 mg of urolithin A. In an embodiment, the nanoparticle composition is administered to the patient at a dose of about 1000 mg of urolithin A.

In an embodiment, the administration is an oral administration. In an embodiment, the oral administration is selected from the group consisting of a tablet, a capsule, a suspension, an emulsion, a syrup, a colloidal dispersion, a dispersion, and an effervescent composition. Oral administration can preferably be performed utilizing a suspension, for example via a reconstituted suspension.

In an embodiment, the administration is a parenteral administration. In an embodiment, the parenteral administration is selected from the group consisting of intravenous, intraarterial, intraperitoneal, intrathecal, intradermal, epidural, intracerebroventricular, intraurethral, intrasternal, intracranial, intratumoral, intramuscular and subcutaneous.

In an embodiment, the nanoparticle composition is administered as a single dose. In an embodiment, the nanoparticle composition is administered as a single unit dose. In an embodiment, the method further comprises administration of a second therapeutic agent to the patient.

In an illustrative aspect, a method of treating one or more symptoms of a kidney injury in a patient in need thereof is provided. The method comprises the step of administering a therapeutically effective amount of a nanoparticle composition to the patient, wherein the nanoparticle composition comprises i) a polymeric nanoparticle, ii) one or more ligands conjugated to the polymeric nanoparticle, and iii) urolithin A, and wherein the administration results in improvement of at least one symptom associated with the kidney injury in the patient The previously described embodiments of the nanoparticle composition, the pharmaceutical composition, and the described methods are also applicable to the method of treating one or more symptoms of a kidney injury.

In an embodiment, the symptoms are selected from the group consisting of weight loss, kidney mass, kidney:body mass, serum creatinine concentration, serum BUN concentration, renal apoptosis, oxidative phosphorylation deficiencies, renal stress, and any combination thereof.

In an illustrative aspect, a method of treating lupus in a patient in need thereof is provided. The method comprises the step of administering a therapeutically effective amount of a nanoparticle composition to the patient, wherein the nanoparticle composition comprises i) a polymeric nanoparticle, ii) one or more ligands conjugated to the polymeric nanoparticle, and iii) urolithin A.

The previously described embodiments of the nanoparticle composition, the pharmaceutical composition, and the described methods are also applicable to the method of treating lupus.

In an embodiment, the method treats one or more symptoms of lupus in a patient. In an embodiment, the symptoms are selected from the group consisting of fatigue, joint pain, joint swelling, inflammation, headache, fever, chest pain, rash, hair loss, and any combination thereof.

In an illustrative aspect, a method of treating an inflammatory disorder in a patient in need thereof is provided. The method comprises the step of administering a therapeutically effective amount of a nanoparticle composition to the patient, wherein the nanoparticle composition comprises i) a polymeric nanoparticle, ii) one or more ligands conjugated to the polymeric nanoparticle, and iii) urolithin A.

The previously described embodiments of the nanoparticle composition, the pharmaceutical composition, and the described methods are also applicable to the method of treating an inflammatory disorder.

In an embodiment, the inflammatory disorder is selected from the group consisting of: alkylosing spondylitis; cervical arthritis; fibromyalgia; gut; juvenile rheumatoid arthritis; lumbosacral arthritis; osteoarthritis; osteoporosis; psoriatic arthritis; rheumatic disease; rheumatoid arthritis; eczema; psoriasis; dermatitis sunburn; inflammatory eye conditions; uveitis; conjunctivitis; inflammatory lung disorders; asthma; bronchitis; ulcers; gingivitis; Crohn's disease; atrophic gastritis; gastritis varialoforme; ulcerative colitis; celiac disease; regional iletis; peptic ulceration; pyresis; inflammation of the GI tract due to *Helicobacter pylori*; visceral inflammation; bladder irritation; cystitis; inflammatory neurological disorders of the central or peripheral nervous system; multiple sclerosis; inflammatory neuropathies; neurological complication of AIDS, and other diseases or disorders associated with inflammation.

In an illustrative aspect, a method of treating an aging-related disorder in a patient in need thereof, said method comprising the step of administering a therapeutically effective amount of a nanoparticle composition to the patient, wherein the nanoparticle composition comprises i) a polymeric nanoparticle, ii) one or more ligands conjugated to the polymeric nanoparticle, and iii) urolithin A.

The previously described embodiments of the nanoparticle composition, the pharmaceutical composition, and the described methods are also applicable to the method of treating an aging-related disorder. For instance, aging-related disorders can be disorders such as Alzheimer's disease (AD) and sarcopenia.

The previously described embodiments of the nanoparticle composition, the pharmaceutical composition, and the described methods are also applicable to the method of treating an aging-related disorder.

The following numbered embodiments are contemplated and are non-limiting:

1. A nanoparticle composition comprising i) a polymeric nanoparticle, ii) one or more ligands conjugated to the polymeric nanoparticle, and iii) urolithin A.
2. The nanoparticle composition of clause 1, any other suitable clause, or any combination of suitable clauses, wherein the polymeric nanoparticle comprises a polymer/copolymer selected from the group consisting of polylactide, poly(lactide-co-glycolide), polycaprolactone, and any combination thereof.
3. The nanoparticle composition of clause 1, any other suitable clause, or any combination of suitable clauses, wherein the ligand is gambogic acid.
4. The nanoparticle composition of clause 1, any other suitable clause, or any combination of suitable clauses, wherein the urolithin A is encapsulated by the polymeric nanoparticle.
5. The nanoparticle composition of clause 1, any other suitable clause, or any combination of suitable clauses, wherein the nanoparticle composition has an average diameter from about 0.5 nm to about 1000 nm.
6. The nanoparticle composition of clause 1, any other suitable clause, or any combination of suitable clauses, wherein the nanoparticle composition has an average diameter from about 1 nm to about 500 nm.
7. The nanoparticle composition of clause 1, any other suitable clause, or any combination of suitable clauses, wherein the nanoparticle composition has an average diameter from about 10 nm to about 400 nm.
8. The nanoparticle composition of clause 1, any other suitable clause, or any combination of suitable clauses, wherein the nanoparticle composition has an average diameter from about 100 nm to about 400 nm.
9. The nanoparticle composition of clause 1, any other suitable clause, or any combination of suitable clauses, wherein the nanoparticle composition has an average diameter from about 100 nm to about 300 nm.
10. The nanoparticle composition of clause 1, any other suitable clause, or any combination of suitable clauses, wherein the nanoparticle composition has an average diameter from about 100 nm to about 200 nm.
11. The nanoparticle composition of clause 1, any other suitable clause, or any combination of suitable clauses, wherein the nanoparticle composition has an average diameter from about 100 nm to about 150 nm.
12. The nanoparticle composition of clause 1, any other suitable clause, or any combination of suitable clauses, wherein the nanoparticle composition has an average diameter from about 200 nm to about 400 nm.
13. The nanoparticle composition of clause 1, any other suitable clause, or any combination of suitable clauses, wherein the nanoparticle composition has an average diameter from about 300 nm to about 400 nm.
14. The nanoparticle composition of clause 1, any other suitable clause, or any combination of suitable clauses, wherein the nanoparticle composition has an average diameter from about 150 nm to about 300 nm.
15. The nanoparticle composition of clause 1, any other suitable clause, or any combination of suitable clauses, wherein the nanoparticle composition has an average diameter from about 150 nm to about 200 nm.
16. The nanoparticle composition of clause 1, any other suitable clause, or any combination of suitable clauses, wherein the nanoparticle composition has an average diameter from about 200 nm to about 300 nm.
17. The nanoparticle composition of clause 1, any other suitable clause, or any combination of suitable clauses, wherein the nanoparticle composition has an average diameter from about 250 nm to about 300 nm.
18. The nanoparticle composition of clause 1, any other suitable clause, or any combination of suitable clauses, wherein the nanoparticle composition is lyophilized.
19. A pharmaceutical composition comprising a nanoparticle composition, wherein the nanoparticle composition comprises i) a polymeric nanoparticle, ii) one or more ligands conjugated to the polymeric nanoparticle, and iii) urolithin A.
20. The pharmaceutical composition of clause 19, any other suitable clause, or any combination of suitable clauses, wherein the pharmaceutical composition is an oral formulation.
21. The pharmaceutical composition of clause 20, any other suitable clause, or any combination of suitable clauses, wherein the oral formulation is selected from the group consisting of a tablet, a capsule, a suspension, an emulsion, a syrup, a colloidal dispersion, a dispersion, and an effervescent composition.
22. The pharmaceutical composition of clause 19, any other suitable clause, or any combination of suitable clauses, wherein the pharmaceutical composition is a parenteral formulation.
23. The pharmaceutical composition of clause 22, any other suitable clause, or any combination of suitable clauses, wherein the parenteral formulation is selected from the group consisting of intravenous, intraarterial, intraperitoneal, intrathecal, intradermal, epidural, intracerebroventricular, intraurethral, intrasternal, intracranial, intratumoral, intramuscular and subcutaneous.
24. The pharmaceutical composition of clause 19, any other suitable clause, or any combination of suitable clauses, wherein the pharmaceutical composition comprises one or more pharmaceutically acceptable carriers.
25. The pharmaceutical composition of clause 19, any other suitable clause, or any combination of suitable clauses, wherein the pharmaceutical composition further comprises a second therapeutic agent.
26. The pharmaceutical composition of clause 19, any other suitable clause, or any combination of suitable clauses, wherein the pharmaceutical composition is formulated as a single dose.
27. The pharmaceutical composition of clause 19, any other suitable clause, or any combination of suitable clauses, wherein the pharmaceutical composition is formulated as a single unit dose.
28. The pharmaceutical composition of clause 19, any other suitable clause, or any combination of suitable clauses, wherein the polymeric nanoparticle comprises a polymer/copolymer selected from the group consisting of polylactide, poly(lactide-co-glycolide), polycaprolactone, and any combination thereof.
29. The pharmaceutical composition of clause 19, any other suitable clause, or any combination of suitable clauses, wherein the ligand is gambogic acid.
30. The pharmaceutical composition of clause 19, any other suitable clause, or any combination of suitable clauses, wherein the urolithin A is encapsulated by the polymeric nanoparticle.
31. The pharmaceutical composition of clause 19, any other suitable clause, or any combination of suitable clauses, wherein the nanoparticle composition has an average diameter from about 0.5 nm to about 1000 nm.
32. The pharmaceutical composition of clause 19, any other suitable clause, or any combination of suitable clauses, wherein the nanoparticle composition has an average diameter from about 1 nm to about 500 nm.
33. The pharmaceutical composition of clause 19, any other suitable clause, or any combination of suitable clauses, wherein the nanoparticle composition has an average diameter from about 10 nm to about 400 nm.
34. The pharmaceutical composition of clause 19, any other suitable clause, or any combination of suitable clauses, wherein the nanoparticle composition has an average diameter from about 100 nm to about 400 nm.
35. The pharmaceutical composition of clause 19, any other suitable clause, or any combination of suitable clauses, wherein the nanoparticle composition has an average diameter from about 100 nm to about 300 nm.
36. The pharmaceutical composition of clause 19, any other suitable clause, or any combination of suitable clauses, wherein the nanoparticle composition has an average diameter from about 100 nm to about 200 nm.
37. The pharmaceutical composition of clause 19, any other suitable clause, or any combination of suitable clauses, wherein the nanoparticle composition has an average diameter from about 100 nm to about 150 nm.
38. The pharmaceutical composition of clause 19, any other suitable clause, or any combination of suitable clauses, wherein the nanoparticle composition has an average diameter from about 200 nm to about 400 nm.
39. The pharmaceutical composition of clause 19, any other suitable clause, or any combination of suitable clauses, wherein the nanoparticle composition has an average diameter from about 300 nm to about 400 nm.
40. The pharmaceutical composition of clause 19, any other suitable clause, or any combination of suitable clauses, wherein the nanoparticle composition has an average diameter from about 150 nm to about 300 nm.
41. The pharmaceutical composition of clause 19, any other suitable clause, or any combination of suitable clauses, wherein the nanoparticle composition has an average diameter from about 150 nm to about 200 nm.
42. The pharmaceutical composition of clause 19, any other suitable clause, or any combination of suitable clauses, wherein the nanoparticle composition has an average diameter from about 200 nm to about 300 nm.
43. The pharmaceutical composition of clause 19, any other suitable clause, or any combination of suitable clauses, wherein the nanoparticle composition has an average diameter from about 250 nm to about 300 nm.
44. A method of treating a kidney injury in a patient in need thereof, said method comprising the step of administering a therapeutically effective amount of a nanoparticle composition to the patient, wherein the nanoparticle composition comprises i) a polymeric nanoparticle, ii) one or more ligands conjugated to the polymeric nanoparticle, and iii) urolithin A.

45. The method of clause 44, any other suitable clause, or any combination of suitable clauses, wherein the kidney injury is an acute kidney injury.
46. The method of clause 44, any other suitable clause, or any combination of suitable clauses, wherein the kidney injury is a chronic kidney injury.
47. The method of clause 44, any other suitable clause, or any combination of suitable clauses, wherein the kidney injury is a drug-induced kidney injury.
48. The method of clause 44, any other suitable clause, or any combination of suitable clauses, wherein the kidney injury is an anticancer drug-induced kidney injury.
49. The method of clause 48, any other suitable clause, or any combination of suitable clauses, wherein the anticancer drug is a platinum-based antineoplastic.
50. The method of clause 48, any other suitable clause, or any combination of suitable clauses, wherein the anticancer drug is cisplatin.
51. The method of clause 48, any other suitable clause, or any combination of suitable clauses, wherein the anticancer drug is carboplatin.
52. The method of clause 48, any other suitable clause, or any combination of suitable clauses, wherein the anticancer drug is oxaliplatin.
53. The method of clause 48, any other suitable clause, or any combination of suitable clauses, wherein the anticancer drug is nedaplatin.
54. The method of clause 44, any other suitable clause, or any combination of suitable clauses, wherein the patient is an animal.
55. The method of clause 54, any other suitable clause, or any combination of suitable clauses, wherein the animal is a mammal.
56. The method of clause 54, any other suitable clause, or any combination of suitable clauses, wherein the animal is a human.
57. The method of clause 44, any other suitable clause, or any combination of suitable clauses, wherein the nanoparticle composition is administered to the patient at a dose of about 0.001 to about 1000 mg of the nanoparticle composition per kg of body weight.
58. The method of clause 44, any other suitable clause, or any combination of suitable clauses, wherein the nanoparticle composition is administered to the patient at a dose of about 0.001 to about 100 mg of the nanoparticle composition per kg of body weight.
59. The method of clause 44, any other suitable clause, or any combination of suitable clauses, wherein the nanoparticle composition is administered to the patient at a dose of about 0.001 to about 10 mg of the nanoparticle composition per kg of body weight.
60. The method of clause 44, any other suitable clause, or any combination of suitable clauses, wherein the nanoparticle composition is administered to the patient at a dose of about 1 to about 5 mg of the nanoparticle composition per kg of body weight.
61. The method of clause 44, any other suitable clause, or any combination of suitable clauses, wherein the nanoparticle composition is administered to the patient at a dose of about 100 mg of urolithin A.
62. The method of clause 44, any other suitable clause, or any combination of suitable clauses, wherein the nanoparticle composition is administered to the patient at a dose of about 250 mg of urolithin A.
63. The method of clause 44, any other suitable clause, or any combination of suitable clauses, wherein the nanoparticle composition is administered to the patient at a dose of about 500 mg of urolithin A.
64. The method of clause 44, any other suitable clause, or any combination of suitable clauses, wherein the nanoparticle composition is administered to the patient at a dose of about 750 mg of urolithin A.
65. The method of clause 44, any other suitable clause, or any combination of suitable clauses, wherein the nanoparticle composition is administered to the patient at a dose of about 1000 mg of urolithin A.
66. The method of clause 44, any other suitable clause, or any combination of suitable clauses, wherein the administration is an oral administration.
67. The method of clause 66, any other suitable clause, or any combination of suitable clauses, wherein the oral administration is selected from the group consisting of a tablet, a capsule, a suspension, an emulsion, a syrup, a colloidal dispersion, a dispersion, and an effervescent composition.
68. The method of clause 44, any other suitable clause, or any combination of suitable clauses, The method of clause 44, any other suitable clause, or any combination of suitable clauses, wherein the administration is a parenteral administration.
69. The method of clause 68, any other suitable clause, or any combination of suitable clauses, wherein the parenteral administration is selected from the group consisting of intravenous, intraarterial, intraperitoneal, intrathecal, intradermal, epidural, intracerebroventricular, intraurethral, intrasternal, intracranial, intratumoral, intramuscular and subcutaneous.
70. The method of clause 44, any other suitable clause, or any combination of suitable clauses, wherein the nanoparticle composition is administered as a single dose.
71. The method of clause 44, any other suitable clause, or any combination of suitable clauses, wherein the nanoparticle composition is administered as a single unit dose.
72. The method of clause 44, any other suitable clause, or any combination of suitable clauses, wherein the method further comprises administration of a second therapeutic agent to the patient.
73. The method of clause 44, any other suitable clause, or any combination of suitable clauses, wherein the polymeric nanoparticle comprises a polymer/copolymer selected from the group consisting of polylactide, poly (lactide-co-glycolide), polycaprolactone, and any combination thereof.
74. The method of clause 44, any other suitable clause, or any combination of suitable clauses, wherein the ligand is gambogic acid.
75. The method of clause 44, any other suitable clause, or any combination of suitable clauses, wherein the urolithin A is encapsulated by the polymeric nanoparticle.
76. The method of clause 44, any other suitable clause, or any combination of suitable clauses, wherein the nanoparticle composition has an average diameter from about 0.5 nm to about 1000 nm.
77. The method of clause 44, any other suitable clause, or any combination of suitable clauses, wherein the nanoparticle composition has an average diameter from about 1 nm to about 500 nm.
78. The method of clause 44, any other suitable clause, or any combination of suitable clauses, wherein the nanoparticle composition has an average diameter from about 10 nm to about 400 nm.

79. The method of clause 44, any other suitable clause, or any combination of suitable clauses, wherein the nanoparticle composition has an average diameter from about 100 nm to about 400 nm.
80. The method of clause 44, any other suitable clause, or any combination of suitable clauses, wherein the nanoparticle composition has an average diameter from about 100 nm to about 300 nm.
81. The method of clause 44, any other suitable clause, or any combination of suitable clauses, wherein the nanoparticle composition has an average diameter from about 100 nm to about 200 nm.
82. The method of clause 44, any other suitable clause, or any combination of suitable clauses, wherein the nanoparticle composition has an average diameter from about 100 nm to about 150 nm.
83. The method of clause 44, any other suitable clause, or any combination of suitable clauses, wherein the nanoparticle composition has an average diameter from about 200 nm to about 400 nm.
84. The method of clause 44, any other suitable clause, or any combination of suitable clauses, wherein the nanoparticle composition has an average diameter from about 300 nm to about 400 nm.
85. The method of clause 44, any other suitable clause, or any combination of suitable clauses, wherein the nanoparticle composition has an average diameter from about 150 nm to about 300 nm.
86. The method of clause 44, any other suitable clause, or any combination of suitable clauses, wherein the nanoparticle composition has an average diameter from about 150 nm to about 200 nm.
87. The method of clause 44, any other suitable clause, or any combination of suitable clauses, wherein the nanoparticle composition has an average diameter from about 200 nm to about 300 nm.
88. The method of clause 44, any other suitable clause, or any combination of suitable clauses, wherein the nanoparticle composition has an average diameter from about 250 nm to about 300 nm.
89. A method of treating one or more symptoms of a kidney injury in a patient, said method comprising the step of administering a therapeutically effective amount of a nanoparticle composition to the patient, wherein the nanoparticle composition comprises i) a polymeric nanoparticle, ii) one or more ligands conjugated to the polymeric nanoparticle, and iii) urolithin A, and wherein the administration results in improvement of at least one symptom associated with the kidney injury in the patient.
90. The method of clause 89, any other suitable clause, or any combination of suitable clauses, wherein the symptoms are selected from the group consisting of weight loss, kidney mass, kidney:body mass, serum creatinine concentration, serum BUN concentration, renal apoptosis, oxidative phosphorylation deficiencies, renal stress, and any combination thereof.
91. The method of clause 89, any other suitable clause, or any combination of suitable clauses, wherein the kidney injury is an acute kidney injury.
92. The method of clause 89, any other suitable clause, or any combination of suitable clauses, wherein the kidney injury is a chronic kidney injury.
93. The method of clause 89, any other suitable clause, or any combination of suitable clauses, wherein the kidney injury is a drug-induced kidney injury.
94. The method of clause 89, any other suitable clause, or any combination of suitable clauses, wherein the kidney injury is an anticancer drug-induced kidney injury.
95. The method of clause 94, any other suitable clause, or any combination of suitable clauses, wherein the anticancer drug is a platinum-based antineoplastic.
96. The method of clause 94, any other suitable clause, or any combination of suitable clauses, wherein the anticancer drug is cisplatin.
97. The method of clause 94, any other suitable clause, or any combination of suitable clauses, wherein the anticancer drug is carboplatin.
98. The method of clause 94, any other suitable clause, or any combination of suitable clauses, wherein the anticancer drug is oxaliplatin.
99. The method of clause 94, any other suitable clause, or any combination of suitable clauses, wherein the anticancer drug is nedaplatin.
100. The method of clause 89, any other suitable clause, or any combination of suitable clauses, wherein the patient is an animal.
101. The method of clause 100, any other suitable clause, or any combination of suitable clauses, wherein the animal is a mammal.
102. The method of clause 100, any other suitable clause, or any combination of suitable clauses, wherein the animal is a human.
103. The method of clause 89, any other suitable clause, or any combination of suitable clauses, wherein the nanoparticle composition is administered to the patient at a dose of about 0.001 to about 1000 mg of the nanoparticle composition per kg of body weight.
104. The method of clause 89, any other suitable clause, or any combination of suitable clauses, wherein the nanoparticle composition is administered to the patient at a dose of about 0.001 to about 100 mg of the nanoparticle composition per kg of body weight.
105. The method of clause 89, any other suitable clause, or any combination of suitable clauses, wherein the nanoparticle composition is administered to the patient at a dose of about 0.001 to about 10 mg of the nanoparticle composition per kg of body weight.
106. The method of clause 89, any other suitable clause, or any combination of suitable clauses, wherein the nanoparticle composition is administered to the patient at a dose of about 1 to about 5 mg of the nanoparticle composition per kg of body weight.
107. The method of clause 89, any other suitable clause, or any combination of suitable clauses, wherein the nanoparticle composition is administered to the patient at a dose of about 100 mg of urolithin A.
108. The method of clause 89, any other suitable clause, or any combination of suitable clauses, wherein the nanoparticle composition is administered to the patient at a dose of about 250 mg of urolithin A.
109. The method of clause 89, any other suitable clause, or any combination of suitable clauses, wherein the nanoparticle composition is administered to the patient at a dose of about 500 mg of urolithin A.
110. The method of clause 89, any other suitable clause, or any combination of suitable clauses, wherein the nanoparticle composition is administered to the patient at a dose of about 750 mg of urolithin A.
111. The method of clause 89, any other suitable clause, or any combination of suitable clauses, wherein the nanoparticle composition is administered to the patient at a dose of about 1000 mg of urolithin A.

112. The method of clause 89, any other suitable clause, or any combination of suitable clauses, wherein the administration is an oral administration.

113. The method of clause 112, any other suitable clause, or any combination of suitable clauses, wherein the oral administration is selected from the group consisting of a tablet, a capsule, a suspension, an emulsion, a syrup, a colloidal dispersion, a dispersion, and an effervescent composition.

114. The method of clause 89, any other suitable clause, or any combination of suitable clauses, wherein the administration is a parenteral administration.

115. The method of clause 114, any other suitable clause, or any combination of suitable clauses, wherein the parenteral administration is selected from the group consisting of intravenous, intraarterial, intraperitoneal, intrathecal, intradermal, epidural, intracerebroventricular, intraurethral, intrasternal, intracranial, intratumoral, intramuscular and subcutaneous.

116. The method of clause 89, any other suitable clause, or any combination of suitable clauses, wherein the nanoparticle composition is administered as a single dose.

117. The method of clause 89, any other suitable clause, or any combination of suitable clauses, wherein the nanoparticle composition is administered as a single unit dose.

118. The method of clause 89, any other suitable clause, or any combination of suitable clauses, wherein the method further comprises administration of a second therapeutic agent to the patient.

119. The method of clause 89, any other suitable clause, or any combination of suitable clauses, wherein the polymeric nanoparticle comprises a polymer/copolymer selected from the group consisting of polylactide, poly(lactide-co-glycolide), polycaprolactone, and any combination thereof.

120. The method of clause 89, any other suitable clause, or any combination of suitable clauses, wherein the ligand is gambogic acid.

121. The method of clause 89, any other suitable clause, or any combination of suitable clauses, wherein the urolithin A is encapsulated by the polymeric nanoparticle.

122. The method of clause 89, any other suitable clause, or any combination of suitable clauses, wherein the nanoparticle composition has an average diameter from about 0.5 nm to about 1000 nm.

123. The method of clause 89, any other suitable clause, or any combination of suitable clauses, wherein the nanoparticle composition has an average diameter from about 1 nm to about 500 nm.

124. The method of clause 89, any other suitable clause, or any combination of suitable clauses, wherein the nanoparticle composition has an average diameter from about 10 nm to about 400 nm.

125. The method of clause 89, any other suitable clause, or any combination of suitable clauses, wherein the nanoparticle composition has an average diameter from about 100 nm to about 400 nm.

126. The method of clause 89, any other suitable clause, or any combination of suitable clauses, wherein the nanoparticle composition has an average diameter from about 100 nm to about 300 nm.

127. The method of clause 89, any other suitable clause, or any combination of suitable clauses, wherein the nanoparticle composition has an average diameter from about 100 nm to about 200 nm.

128. The method of clause 89, any other suitable clause, or any combination of suitable clauses, wherein the nanoparticle composition has an average diameter from about 100 nm to about 150 nm.

129. The method of clause 89, any other suitable clause, or any combination of suitable clauses, wherein the nanoparticle composition has an average diameter from about 200 nm to about 400 nm.

130. The method of clause 89, any other suitable clause, or any combination of suitable clauses, wherein the nanoparticle composition has an average diameter from about 300 nm to about 400 nm.

131. The method of clause 89, any other suitable clause, or any combination of suitable clauses, wherein the nanoparticle composition has an average diameter from about 150 nm to about 300 nm.

132. The method of clause 89, any other suitable clause, or any combination of suitable clauses, wherein the nanoparticle composition has an average diameter from about 150 nm to about 200 nm.

133. The method of clause 89, any other suitable clause, or any combination of suitable clauses, wherein the nanoparticle composition has an average diameter from about 200 nm to about 300 nm.

134. The method of clause 89, any other suitable clause, or any combination of suitable clauses, wherein the nanoparticle composition has an average diameter from about 250 nm to about 300 nm.

135. A method of treating lupus in a patient in need thereof, said method comprising the step of administering a therapeutically effective amount of a nanoparticle composition to the patient, wherein the nanoparticle composition comprises i) a polymeric nanoparticle, ii) one or more ligands conjugated to the polymeric nanoparticle, and iii) urolithin A.

136. The method of clause 135, any other suitable clause, or any combination of suitable clauses, wherein the method treats one or more symptoms of lupus in a patient.

137. The method of clause 136, any other suitable clause, or any combination of suitable clauses, wherein the symptoms are selected from the group consisting of fatigue, joint pain, joint swelling, inflammation, headache, fever, chest pain, rash, hair loss, and any combination thereof.

138. The method of clause 135, any other suitable clause, or any combination of suitable clauses, wherein the patient is an animal.

139. The method of clause 138, any other suitable clause, or any combination of suitable clauses, wherein the animal is a mammal.

140. The method of clause 138, any other suitable clause, or any combination of suitable clauses, wherein the animal is a human.

141. The method of clause 135, any other suitable clause, or any combination of suitable clauses, wherein the nanoparticle composition is administered to the patient at a dose of about 0.001 to about 1000 mg of the nanoparticle composition per kg of body weight.

142. The method of clause 135, any other suitable clause, or any combination of suitable clauses, wherein the nanoparticle composition is administered to the patient at a dose of about 0.001 to about 100 mg of the nanoparticle composition per kg of body weight.

143. The method of clause 135, any other suitable clause, or any combination of suitable clauses, wherein the nanoparticle composition is administered to the patient at a dose of about 0.001 to about 10 mg of the nanoparticle composition per kg of body weight.
144. The method of clause 135, any other suitable clause, or any combination of suitable clauses, wherein the nanoparticle composition is administered to the patient at a dose of about 1 to about 5 mg of the nanoparticle composition per kg of body weight.
145. The method of clause 135, any other suitable clause, or any combination of suitable clauses, wherein the nanoparticle composition is administered to the patient at a dose of about 100 mg of urolithin A.
146. The method of clause 135, any other suitable clause, or any combination of suitable clauses, wherein the nanoparticle composition is administered to the patient at a dose of about 250 mg of urolithin A.
147. The method of clause 135, any other suitable clause, or any combination of suitable clauses, wherein the nanoparticle composition is administered to the patient at a dose of about 500 mg of urolithin A.
148. The method of clause 135, any other suitable clause, or any combination of suitable clauses, wherein the nanoparticle composition is administered to the patient at a dose of about 750 mg of urolithin A.
149. The method of clause 135, any other suitable clause, or any combination of suitable clauses, wherein the nanoparticle composition is administered to the patient at a dose of about 1000 mg of urolithin A.
150. The method of clause 135, any other suitable clause, or any combination of suitable clauses, wherein the administration is an oral administration.
151. The method of clause 150, any other suitable clause, or any combination of suitable clauses, wherein the oral administration is selected from the group consisting of a tablet, a capsule, a suspension, an emulsion, a syrup, a colloidal dispersion, a dispersion, and an effervescent composition.
152. The method of clause 135, any other suitable clause, or any combination of suitable clauses, wherein the administration is a parenteral administration.
153. The method of clause 152, any other suitable clause, or any combination of suitable clauses, wherein the parenteral administration is selected from the group consisting of intravenous, intraarterial, intraperitoneal, intrathecal, intradermal, epidural, intracerebroventricular, intraurethral, intrasternal, intracranial, intratumoral, intramuscular and subcutaneous.
154. The method of clause 135, any other suitable clause, or any combination of suitable clauses, wherein the nanoparticle composition is administered as a single dose.
155. The method of clause 135, any other suitable clause, or any combination of suitable clauses, wherein the nanoparticle composition is administered as a single unit dose.
156. The method of clause 135, any other suitable clause, or any combination of suitable clauses, wherein the method further comprises administration of a second therapeutic agent to the patient.
157. The method of clause 135, any other suitable clause, or any combination of suitable clauses, wherein the polymeric nanoparticle comprises a polymer/copolymer selected from the group consisting of polylactide, poly(lactide-co-glycolide), polycaprolactone, and any combination thereof.
158. The method of clause 135, any other suitable clause, or any combination of suitable clauses, wherein the ligand is gambogic acid.
159. The method of clause 135, any other suitable clause, or any combination of suitable clauses, wherein the urolithin A is encapsulated by the polymeric nanoparticle.
160. The method of clause 135, any other suitable clause, or any combination of suitable clauses, wherein the nanoparticle composition has an average diameter from about 0.5 nm to about 1000 nm.
161. The method of clause 135, any other suitable clause, or any combination of suitable clauses, wherein the nanoparticle composition has an average diameter from about 1 nm to about 500 nm.
162. The method of clause 135, any other suitable clause, or any combination of suitable clauses, wherein the nanoparticle composition has an average diameter from about 10 nm to about 400 nm.
163. The method of clause 135, any other suitable clause, or any combination of suitable clauses, wherein the nanoparticle composition has an average diameter from about 100 nm to about 400 nm.
164. The method of clause 135, any other suitable clause, or any combination of suitable clauses, wherein the nanoparticle composition has an average diameter from about 100 nm to about 300 nm.
165. The method of clause 135, any other suitable clause, or any combination of suitable clauses, wherein the nanoparticle composition has an average diameter from about 100 nm to about 200 nm.
166. The method of clause 135, any other suitable clause, or any combination of suitable clauses, wherein the nanoparticle composition has an average diameter from about 100 nm to about 150 nm.
167. The method of clause 135, any other suitable clause, or any combination of suitable clauses, wherein the nanoparticle composition has an average diameter from about 200 nm to about 400 nm.
168. The method of clause 135, any other suitable clause, or any combination of suitable clauses, wherein the nanoparticle composition has an average diameter from about 300 nm to about 400 nm.
169. The method of clause 135, any other suitable clause, or any combination of suitable clauses, wherein the nanoparticle composition has an average diameter from about 150 nm to about 300 nm.
170. The method of clause 135, any other suitable clause, or any combination of suitable clauses, wherein the nanoparticle composition has an average diameter from about 150 nm to about 200 nm.
171. The method of clause 135, any other suitable clause, or any combination of suitable clauses, wherein the nanoparticle composition has an average diameter from about 200 nm to about 300 nm.
172. The method of clause 135, any other suitable clause, or any combination of suitable clauses, wherein the nanoparticle composition has an average diameter from about 250 nm to about 300 nm.
173. A method of treating an inflammatory disorder in a patient in need thereof, said method comprising the step of administering a therapeutically effective amount of a nanoparticle composition to the patient, wherein the nanoparticle composition comprises i) a polymeric nanoparticle, ii) one or more ligands conjugated to the polymeric nanoparticle, and iii) urolithin A.

174. The method of clause 173, any other suitable clause, or any combination of suitable clauses, wherein the inflammatory disorder is selected from the group consisting of: alkylosing spondylitis; cervical arthritis; fibromyalgia; gut; juvenile rheumatoid arthritis; lumbosacral arthritis; osteoarthritis; osteoporosis; psoriatic arthritis; rheumatic disease; rheumatoid arthritis; eczema; psoriasis; dermatitis sunburn; inflammatory eye conditions; uveitis; conjunctivitis; inflammatory lung disorders; asthma; bronchitis; ulcers; gingivitis; Crohn's disease; atrophic gastritis; gastritis varialoforme; ulcerative colitis; celiac disease; regional iletis; peptic ulceration; pyresis; inflammation of the GI tract due to *Helicobacter pylori*; visceral inflammation; bladder irritation; cystitis; inflammatory neurological disorders of the central or peripheral nervous system; multiple sclerosis; inflammatory neuropathies; neurological complication of AIDS, and other diseases or disorders associated with inflammation.

175. The method of clause 173, any other suitable clause, or any combination of suitable clauses, wherein the patient is an animal.

176. The method of clause 175, any other suitable clause, or any combination of suitable clauses, wherein the animal is a mammal.

177. The method of clause 175, any other suitable clause, or any combination of suitable clauses, wherein the animal is a human.

178. The method of clause 173, any other suitable clause, or any combination of suitable clauses, wherein the nanoparticle composition is administered to the patient at a dose of about 0.001 to about 1000 mg of the nanoparticle composition per kg of body weight.

179. The method of clause 173, any other suitable clause, or any combination of suitable clauses, wherein the nanoparticle composition is administered to the patient at a dose of about 0.001 to about 100 mg of the nanoparticle composition per kg of body weight.

180. The method of clause 173, any other suitable clause, or any combination of suitable clauses, wherein the nanoparticle composition is administered to the patient at a dose of about 0.001 to about 10 mg of the nanoparticle composition per kg of body weight.

181. The method of clause 173, any other suitable clause, or any combination of suitable clauses, wherein the nanoparticle composition is administered to the patient at a dose of about 1 to about 5 mg of the nanoparticle composition per kg of body weight.

182. The method of clause 173, any other suitable clause, or any combination of suitable clauses, wherein the nanoparticle composition is administered to the patient at a dose of about 100 mg of urolithin A.

183. The method of clause 173, any other suitable clause, or any combination of suitable clauses, wherein the nanoparticle composition is administered to the patient at a dose of about 250 mg of urolithin A.

184. The method of clause 173, any other suitable clause, or any combination of suitable clauses, wherein the nanoparticle composition is administered to the patient at a dose of about 500 mg of urolithin A.

185. wherein the nanoparticle composition is administered to the patient at a dose of The method of clause 173, any other suitable clause, or any combination of suitable clauses, about 750 mg of urolithin A.

186. The method of clause 173, any other suitable clause, or any combination of suitable clauses, wherein the nanoparticle composition is administered to the patient at a dose of about 1000 mg of urolithin A.

187. The method of clause 173, any other suitable clause, or any combination of suitable clauses, wherein the administration is an oral administration.

188. The method of clause 187, any other suitable clause, or any combination of suitable clauses, wherein the oral administration is selected from the group consisting of a tablet, a capsule, a suspension, an emulsion, a syrup, a colloidal dispersion, a dispersion, and an effervescent composition.

189. The method of clause 173, any other suitable clause, or any combination of suitable clauses, wherein the administration is a parenteral administration.

190. The method of clause 189, any other suitable clause, or any combination of suitable clauses, wherein the parenteral administration is selected from the group consisting of intravenous, intraarterial, intraperitoneal, intrathecal, intradermal, epidural, intracerebroventricular, intraurethral, intrasternal, intracranial, intratumoral, intramuscular and subcutaneous.

191. The method of clause 173, any other suitable clause, or any combination of suitable clauses, wherein the nanoparticle composition is administered as a single dose.

192. The method of clause 173, any other suitable clause, or any combination of suitable clauses, wherein the nanoparticle composition is administered as a single unit dose.

193. The method of clause 173, any other suitable clause, or any combination of suitable clauses, wherein the method further comprises administration of a second therapeutic agent to the patient.

194. The method of clause 173, any other suitable clause, or any combination of suitable clauses, wherein the polymeric nanoparticle comprises a polymer/copolymer selected from the group consisting of polylactide, poly(lactide-co-glycolide), polycaprolactone, and any combination thereof.

195. The method of clause 173, any other suitable clause, or any combination of suitable clauses, wherein the ligand is gambogic acid.

196. The method of clause 173, any other suitable clause, or any combination of suitable clauses, wherein the urolithin A is encapsulated by the polymeric nanoparticle.

197. The method of clause 173, any other suitable clause, or any combination of suitable clauses, wherein the nanoparticle composition has an average diameter from about 0.5 nm to about 1000 nm.

198. The method of clause 173, any other suitable clause, or any combination of suitable clauses, wherein the nanoparticle composition has an average diameter from about 1 nm to about 500 nm.

199. The method of clause 173, any other suitable clause, or any combination of suitable clauses, wherein the nanoparticle composition has an average diameter from about 10 nm to about 400 nm.

200. The method of clause 173, any other suitable clause, or any combination of suitable clauses, wherein the nanoparticle composition has an average diameter from about 100 nm to about 400 nm.

201. The method of clause 173, any other suitable clause, or any combination of suitable clauses, wherein the nanoparticle composition has an average diameter from about 100 nm to about 300 nm.

202. The method of clause 173, any other suitable clause, or any combination of suitable clauses, wherein the nanoparticle composition has an average diameter from about 100 nm to about 200 nm.
203. The method of clause 173, any other suitable clause, or any combination of suitable clauses, wherein the nanoparticle composition has an average diameter from about 100 nm to about 150 nm.
204. The method of clause 173, any other suitable clause, or any combination of suitable clauses, wherein the nanoparticle composition has an average diameter from about 200 nm to about 400 nm.
205. The method of clause 173, any other suitable clause, or any combination of suitable clauses, wherein the nanoparticle composition has an average diameter from about 300 nm to about 400 nm.
206. The method of clause 173, any other suitable clause, or any combination of suitable clauses, wherein the nanoparticle composition has an average diameter from about 150 nm to about 300 nm.
207. The method of clause 173, any other suitable clause, or any combination of suitable clauses, wherein the nanoparticle composition has an average diameter from about 150 nm to about 200 nm.
208. The method of clause 173, any other suitable clause, or any combination of suitable clauses, wherein the nanoparticle composition has an average diameter from about 200 nm to about 300 nm.
209. The method of clause 173, any other suitable clause, or any combination of suitable clauses, wherein the nanoparticle composition has an average diameter from about 250 nm to about 300 nm.
210. A method of treating an aging-related disorder in a patient in need thereof, said method comprising the step of administering a therapeutically effective amount of a nanoparticle composition to the patient, wherein the nanoparticle composition comprises i) a polymeric nanoparticle, ii) one or more ligands conjugated to the polymeric nanoparticle, and iii) urolithin A.
211. The method of clause 210, any other suitable clause, or any combination of suitable clauses, wherein the patient is an animal.
212. The method of clause 211, any other suitable clause, or any combination of suitable clauses, wherein the animal is a mammal.
213. The method of clause 211, any other suitable clause, or any combination of suitable clauses, wherein the animal is a human.
214. The method of clause 210, any other suitable clause, or any combination of suitable clauses, wherein the nanoparticle composition is administered to the patient at a dose of about 0.001 to about 1000 mg of the nanoparticle composition per kg of body weight.
215. The method of clause 210, any other suitable clause, or any combination of suitable clauses, wherein the nanoparticle composition is administered to the patient at a dose of about 0.001 to about 100 mg of the nanoparticle composition per kg of body weight.
216. The method of clause 210, any other suitable clause, or any combination of suitable clauses, wherein the nanoparticle composition is administered to the patient at a dose of about 0.001 to about 10 mg of the nanoparticle composition per kg of body weight.
217. The method of clause 210, any other suitable clause, or any combination of suitable clauses, wherein the nanoparticle composition is administered to the patient at a dose of about 1 to about 5 mg of the nanoparticle composition per kg of body weight.
218. The method of clause 210, any other suitable clause, or any combination of suitable clauses, wherein the nanoparticle composition is administered to the patient at a dose of about 100 mg of urolithin A.
219. The method of clause 210, any other suitable clause, or any combination of suitable clauses, wherein the nanoparticle composition is administered to the patient at a dose of about 250 mg of urolithin A.
220. The method of clause 210, any other suitable clause, or any combination of suitable clauses, wherein the nanoparticle composition is administered to the patient at a dose of about 500 mg of urolithin A.
221. The method of clause 210, any other suitable clause, or any combination of suitable clauses, wherein the nanoparticle composition is administered to the patient at a dose of about 750 mg of urolithin A.
222. The method of clause 210, any other suitable clause, or any combination of suitable clauses, wherein the nanoparticle composition is administered to the patient at a dose of about 1000 mg of urolithin A.
223. The method of clause 210, any other suitable clause, or any combination of suitable clauses, wherein the administration is an oral administration.
224. The method of clause 223, any other suitable clause, or any combination of suitable clauses, wherein the oral administration is selected from the group consisting of a tablet, a capsule, a suspension, an emulsion, a syrup, a colloidal dispersion, a dispersion, and an effervescent composition.
225. The method of clause 210, any other suitable clause, or any combination of suitable clauses, wherein the administration is a parenteral administration.
226. The method of clause 225, any other suitable clause, or any combination of suitable clauses, wherein the parenteral administration is selected from the group consisting of intravenous, intraarterial, intraperitoneal, intrathecal, intradermal, epidural, intracerebroventricular, intraurethral, intrasternal, intracranial, intratumoral, intramuscular and subcutaneous.
227. The method of clause 210, any other suitable clause, or any combination of suitable clauses, wherein the nanoparticle composition is administered as a single dose.
228. The method of clause 210, any other suitable clause, or any combination of suitable clauses, wherein the nanoparticle composition is administered as a single unit dose.
229. The method of clause 210, any other suitable clause, or any combination of suitable clauses, wherein the method further comprises administration of a second therapeutic agent to the patient.
230. The method of clause 210, any other suitable clause, or any combination of suitable clauses, wherein the polymeric nanoparticle comprises a polymer/copolymer selected from the group consisting of polylactide, poly(lactide-co-glycolide), polycaprolactone, and any combination thereof.
231. The method of clause 210, any other suitable clause, or any combination of suitable clauses, wherein the ligand is gambogic acid.
232. The method of clause 210, any other suitable clause, or any combination of suitable clauses, wherein the urolithin A is encapsulated by the polymeric nanoparticle.

233. The method of clause 210, any other suitable clause, or any combination of suitable clauses, wherein the nanoparticle composition has an average diameter from about 0.5 nm to about 1000 nm.
234. The method of clause 210, any other suitable clause, or any combination of suitable clauses, wherein the nanoparticle composition has an average diameter from about 1 nm to about 500 nm.
235. The method of clause 210, any other suitable clause, or any combination of suitable clauses, wherein the nanoparticle composition has an average diameter from about 10 nm to about 400 nm.
236. The method of clause 210, any other suitable clause, or any combination of suitable clauses, wherein the nanoparticle composition has an average diameter from about 100 nm to about 400 nm.
237. The method of clause 210, any other suitable clause, or any combination of suitable clauses, wherein the nanoparticle composition has an average diameter from about 100 nm to about 300 nm.
238. The method of clause 210, any other suitable clause, or any combination of suitable clauses, wherein the nanoparticle composition has an average diameter from about 100 nm to about 200 nm.
239. The method of clause 210, any other suitable clause, or any combination of suitable clauses, wherein the nanoparticle composition has an average diameter from about 100 nm to about 150 nm.
240. The method of clause 210, any other suitable clause, or any combination of suitable clauses, wherein the nanoparticle composition has an average diameter from about 200 nm to about 400 nm.
241. The method of clause 210, any other suitable clause, or any combination of suitable clauses, wherein the nanoparticle composition has an average diameter from about 300 nm to about 400 nm.
242. The method of clause 210, any other suitable clause, or any combination of suitable clauses, wherein the nanoparticle composition has an average diameter from about 150 nm to about 300 nm.
243. The method of clause 210, any other suitable clause, or any combination of suitable clauses, wherein the nanoparticle composition has an average diameter from about 150 nm to about 200 nm.
244. The method of clause 210, any other suitable clause, or any combination of suitable clauses, wherein the nanoparticle composition has an average diameter from about 200 nm to about 300 nm.
245. The method of clause 210, any other suitable clause, or any combination of suitable clauses, wherein the nanoparticle composition has an average diameter from about 250 nm to about 300 nm.
246. A method of treating cancer in a patient in need thereof, said method comprising:
    a) administering a therapeutically effective amount of a nanoparticle composition to the patient, wherein the nanoparticle composition comprises i) a polymeric nanoparticle, ii) one or more ligands conjugated to the polymeric nanoparticle, and iii) urolithin A, and
    b) administering a therapeutically effective amount of cisplatin to the patient.
247. The method of clause 246, any other suitable clause, or any combination of suitable clauses, wherein the patient is an animal.
248. The method of clause 247, any other suitable clause, or any combination of suitable clauses, wherein the animal is a mammal.
249. The method of clause 247, any other suitable clause, or any combination of suitable clauses, wherein the animal is a human.
250. The method of clause 246, any other suitable clause, or any combination of suitable clauses, wherein the nanoparticle composition is administered to the patient at a dose of about 0.001 to about 1000 mg of the nanoparticle composition per kg of body weight.
251. The method of clause 246, any other suitable clause, or any combination of suitable clauses, wherein the nanoparticle composition is administered to the patient at a dose of about 0.001 to about 100 mg of the nanoparticle composition per kg of body weight.
252. The method of clause 246, any other suitable clause, or any combination of suitable clauses, wherein the nanoparticle composition is administered to the patient at a dose of about 0.001 to about 10 mg of the nanoparticle composition per kg of body weight.
253. The method of clause 246, any other suitable clause, or any combination of suitable clauses, wherein the nanoparticle composition is administered to the patient at a dose of about 1 to about 5 mg of the nanoparticle composition per kg of body weight.
254. The method of clause 246, any other suitable clause, or any combination of suitable clauses, wherein the nanoparticle composition is administered to the patient at a dose of about 100 mg of urolithin A.
255. The method of clause 246, any other suitable clause, or any combination of suitable clauses, wherein the nanoparticle composition is administered to the patient at a dose of about 250 mg of urolithin A.
256. The method of clause 246, any other suitable clause, or any combination of suitable clauses, wherein the nanoparticle composition is administered to the patient at a dose of about 500 mg of urolithin A.
257. The method of clause 246, any other suitable clause, or any combination of suitable clauses, wherein the nanoparticle composition is administered to the patient at a dose of about 750 mg of urolithin A.
258. The method of clause 246, any other suitable clause, or any combination of suitable clauses, wherein the nanoparticle composition is administered to the patient at a dose of about 1000 mg of urolithin A.
259. The method of clause 246, any other suitable clause, or any combination of suitable clauses, wherein the administration is an oral administration.
260. The method of clause 259, any other suitable clause, or any combination of suitable clauses, wherein the oral administration is selected from the group consisting of a tablet, a capsule, a suspension, an emulsion, a syrup, a colloidal dispersion, a dispersion, and an effervescent composition.
261. The method of clause 246, any other suitable clause, or any combination of suitable clauses, wherein the administration is a parenteral administration.
262. The method of clause 261, any other suitable clause, or any combination of suitable clauses, wherein the parenteral administration is selected from the group consisting of intravenous, intraarterial, intraperitoneal, intrathecal, intradermal, epidural, intracerebroventricular, intraurethral, intrasternal, intracranial, intratumoral, intramuscular and subcutaneous.
263. The method of clause 246, any other suitable clause, or any combination of suitable clauses, wherein the nanoparticle composition is administered as a single dose.

264. The method of clause 246, any other suitable clause, or any combination of suitable clauses, wherein the nanoparticle composition is administered as a single unit dose.
265. The method of clause 246, any other suitable clause, or any combination of suitable clauses, wherein the method further comprises administration of a second therapeutic agent to the patient.
266. The method of clause 246, any other suitable clause, or any combination of suitable clauses, wherein the polymeric nanoparticle comprises a polymer/copolymer selected from the group consisting of polylactide, poly(lactide-co-glycolide), polycaprolactone, and any combination thereof.
267. The method of clause 246, any other suitable clause, or any combination of suitable clauses, wherein the ligand is gambogic acid.
268. The method of clause 246, any other suitable clause, or any combination of suitable clauses, wherein the urolithin A is encapsulated by the polymeric nanoparticle.
269. The method of clause 246, any other suitable clause, or any combination of suitable clauses, wherein the nanoparticle composition has an average diameter from about 0.5 nm to about 1000 nm.
270. The method of clause 246, any other suitable clause, or any combination of suitable clauses, wherein the nanoparticle composition has an average diameter from about 1 nm to about 500 nm.
271. The method of clause 246, any other suitable clause, or any combination of suitable clauses, wherein the nanoparticle composition has an average diameter from about 10 nm to about 400 nm.
272. The method of clause 246, any other suitable clause, or any combination of suitable clauses, wherein the nanoparticle composition has an average diameter from about 100 nm to about 400 nm.
273. The method of clause 246, any other suitable clause, or any combination of suitable clauses, wherein the nanoparticle composition has an average diameter from about 100 nm to about 300 nm.
274. The method of clause 246, any other suitable clause, or any combination of suitable clauses, wherein the nanoparticle composition has an average diameter from about 100 nm to about 200 nm.
275. The method of clause 246, any other suitable clause, or any combination of suitable clauses, wherein the nanoparticle composition has an average diameter from about 100 nm to about 150 nm.
276. The method of clause 246, any other suitable clause, or any combination of suitable clauses, wherein the nanoparticle composition has an average diameter from about 200 nm to about 400 nm.
277. The method of clause 246, any other suitable clause, or any combination of suitable clauses, wherein the nanoparticle composition has an average diameter from about 300 nm to about 400 nm.
278. The method of clause 246, any other suitable clause, or any combination of suitable clauses, wherein the nanoparticle composition has an average diameter from about 150 nm to about 300 nm.
279. The method of clause 246, any other suitable clause, or any combination of suitable clauses, wherein the nanoparticle composition has an average diameter from about 150 nm to about 200 nm.
280. The method of clause 246, any other suitable clause, or any combination of suitable clauses, wherein the nanoparticle composition has an average diameter from about 200 nm to about 300 nm.
281. The method of clause 246, any other suitable clause, or any combination of suitable clauses, wherein the nanoparticle composition has an average diameter from about 250 nm to about 300 nm.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Example 1

Nanoparticle Encapsulation of Urolithin A and Bioavailability of Nanoparticle Compositions To determine whether precision polymer nanosystems (P2Ns) could improve the oral bioavailability of urolithin A (UA), UA was encapsulated using the emulsion-diffusion-evaporation method in either unconjugated (P2Ns) or GA-conjugated (P2Ns-GA) formats.

Materials

All reagents were analytical grade, unless mentioned otherwise, and were obtained from Fisher Scientific (Hampton, N.H.). Cis-diamminedichloridoplatinum or cisplatin (CIS) was obtained from Shaanxi Sciphar Hi-Tech Industry Co Ltd. (Xi'an, China). (Di-n-dodecyl)-dimethylammonium bromide (DMAB) was obtained from Alfa Aesar (Ward Hill, Mass.). Urolithin A was obtained from Angene (London, England). Gambogic acid was obtained from BroadPharm (San Diego Calif.).

Polymer Synthesis and Preparation of Nanoparticle Compositions Comprising UA

Briefly, polymers with or without gambogic acid (GA) conjugation were prepared. Assembly of polymers into nanoparticles and the concurrent encapsulation of UA was accomplished using the oil-in-water emulsification method. Methods for formulation of nanoparticle compositions using polymer/copolymer and/or GA can be found, for example, in U.S. Patent Application Publication No. 2018/0110865 and U.S. Patent Application Publication No. 2018/0214386, both herein incorporated by reference in their entireties.

The amount and efficiency of UA encapsulation were determined by LC-MS as is well known in the art. Nanoparticle particle size and shape were evaluated by dynamic light scattering (DLS) and scanning electron microscopy (SEM) according to art-recognized methods. All nanoparticle compositions were lyophilized for storage and reconstituted with sucrose solution prior to use.

UA Pharmacokinetics Study

Male Sprague/Dawley rats (200-300 g) were obtained from Envigo (Huntingdon, England). Animals were divided into four groups with four animals per group; each animal receiving by oral gavage a single dose of i) 50 mg plain UA, ii) 25 mg P2Ns/UA nanoparticle composition, iii) 10 mg P2Ns-GA/UA nanoparticle composition, or iv) 25 mg P2Ns-GA/UA nanoparticle composition. Plasma samples were prepared from tail vein blood collected at 0-48 hours post-dosing. UA concentrations were determined by LC-MS.

Overall, an entrapment efficiency of approximately 35% was achieved in both nanoparticle formats. Evaluation of particle properties such as size, shape, polydispersity index (PDI), pH, and ζ-potential revealed that UA loading had not significantly altered the P2Ns/UA nanoparticle composition characteristics (see FIGS. 1A-1B).

The pharmacokinetics of P2Ns nanoparticle composition and P2Ns-GA/UA nanoparticle composition were compared to plain UA in the healthy rat model. An oral dose of 50 mg/kg was chosen for plain UA to serve as the baseline in the bioavailability study. Serum $C_{max}$ (peak concentration) and AUC (area under curve) of the P2Ns/UA nanoparticle compositions were moderately increased (2-fold change) over plain UA (see FIGS. 1C-1D). In contrast, the P2Ns-GA/UA nanoparticle compositions exhibited significantly better bioavailability, with about 7-fold change in serum $C_{max}$ and AUC compared to plain UA (see FIGS. 1C-1D). Due to the superiority of P2Ns-GA/UA nanoparticle compositions in the oral delivery of UA, the therapeutic potential of these nanoparticle compositions was evaluated in a cisplatin-induced model of acute kidney injury.

Example 2

Mouse Survival Analysis of Nanoparticle Compositions

CIS-Induced Acute Kidney Injury Model

Male C57BL/6J mice (8-10 weeks) were obtained from Jackson Laboratory (Bay Harbor, Me.). Mice were divided into three groups: cisplatin ("CIS") control (n=8), P2Ns-GA/UA nanoparticle composition (n=8), and Negative control (n=4). To begin the survival study, each mouse in the CIS control and P2Ns-GA/UA nanoparticle composition groups received 20 mg/kg of CIS dissolved in saline via IP injection. Regular dosing of P2Ns-GA/UA nanoparticle composition at 50 mg/kg was administered by oral gavage to each mouse of this group three times per week up to 19 days. Mice were monitored daily by the veterinary staff, and were euthanized immediately when threshold criteria for morbidity were met.

Biochemical Analyses

At euthanasia, mouse blood was collected by cardiac puncture and centrifuged to obtain the plasma. Approximately 75 μL of plasma per mice from four to five mice per group was sent to Texas A&M Veterinary Medical Diagnostic Laboratory (TVMDL) for creatinine and blood urine nitrogen (BUN) quantification.

For the survival study, two groups of male C57BL/6J mice (n=8 per group) were each given a single intraperitoneal dose (20 mg/kg) of CIS known to cause lethal acute kidney injury ("AKI"). The P2Ns-GA/UA nanoparticle compositions (P2Ns-GA UA) were then administered via oral gavage to the treatment group, whereas the CIS control group received no further dosing. Age and gender-matched C57BL/6J mice without CIS or UA treatment (n=4) were used as negative controls. Mice were monitored daily, and were sacrificed immediately when pre-established criteria for morbidity were met or upon study termination (day 19).

Figure 2A:
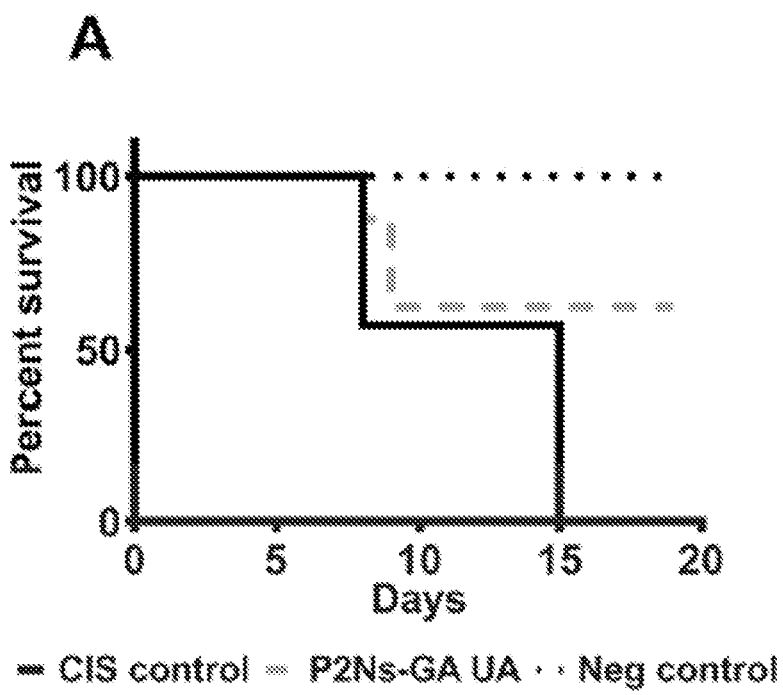
FIGS. 2A-2D show the effect of P2Ns-GA UA nanoparticle compositions on mouse survival and other physiological markers after cisplatin-induced acute kidney injury ("CIS-induced AKI").

However, some mice prematurely died before receiving euthanasia and having their organs harvested. The CIS control group began dying by day 8, with 100% death by day 15. In contrast, treatment with P2Ns-GA UA was found to have a positive effect on survival, delaying the onset of death by 1 day in those that died and reducing overall mortality by 63% (see FIG. 2A). Furthermore, mice that survived in the P2Ns-GA UA group appeared healthy at day 19, suggesting that they may have been recovering from CIS-induced injuries.

Figure 2B:
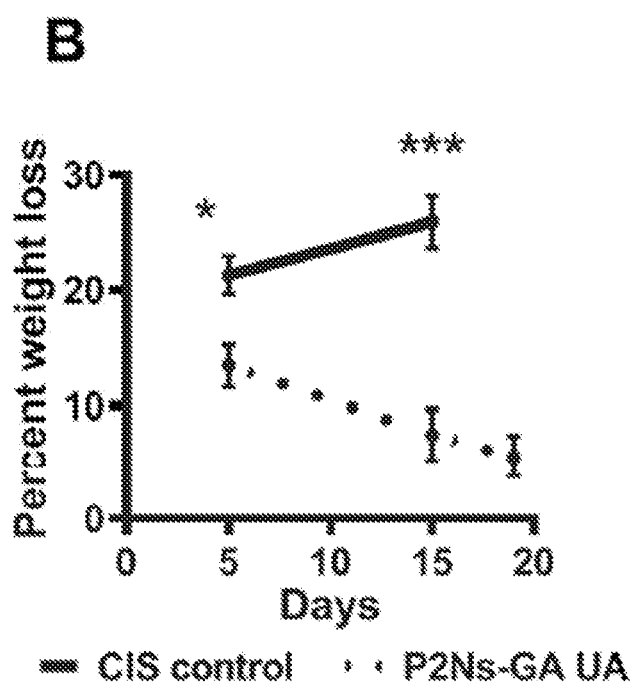
Figure 2C:
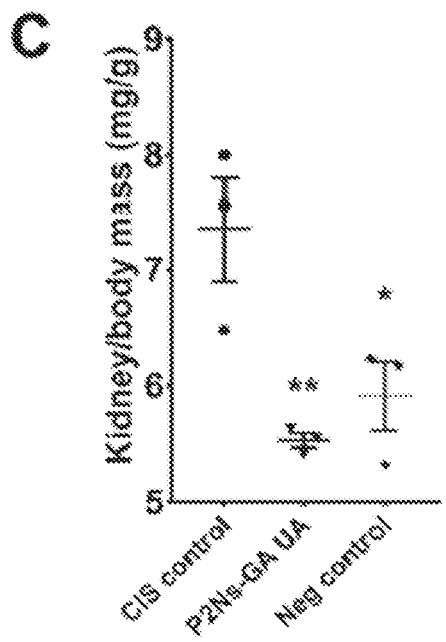
Figure 2D:
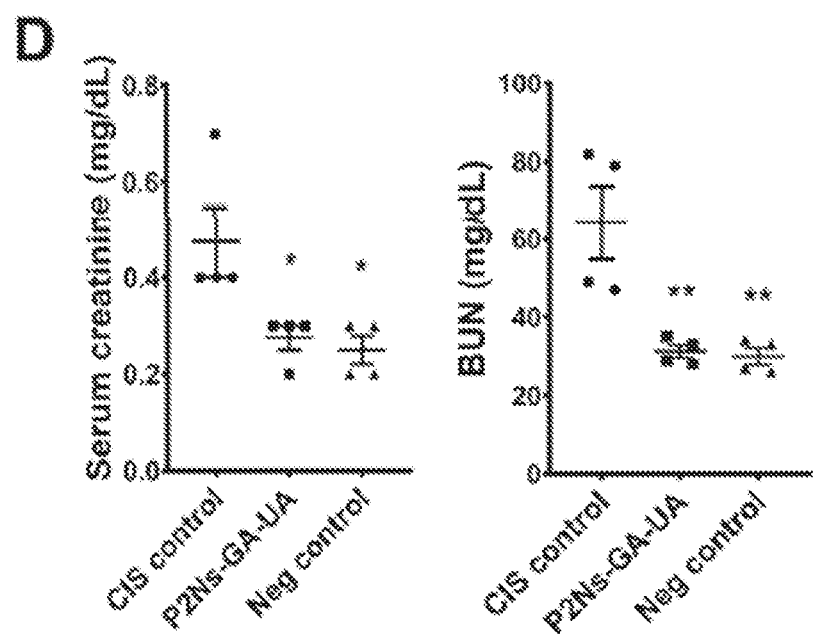

The P2Ns-GA UA group also displayed progressively less reduction in weight loss following CIS injection and had no discernable changes in kidney mass to-body weight ratio at sacrifice (see FIG. 2B-2C). Finally, BUN and serum creatinine concentrations of sacrificed mice (15-19 days) showed that these parameters had returned to normal for P2Ns-GA UA treated mice, whereas they were still significantly elevated for the CIS control group (see FIG. 2D). Kidney tissues from both early (8-9 days) and late (15-19 days) sacrificed mice were harvested and used for subsequent analyses.

Example 3

Efficacy of Nanoparticle Compositions in Treatment of Kidney Injury

Histopathology

With exception to animals that died before euthanasia was given, all tissues were dissected from mice and immediately placed in 10% formalin for at least 2 weeks for fixation. Formalin fixed and paraffin embedded kidney sections (~5 micron thickness) were stained by hematoxylin and eosin as well as periodic acid-Schiff reagents. Images were captured using a bright-field microscope at 4× and 40× magnification (Accu-Scope Commack, NY). Five representative images taken from different mice within the same group were subjected to ImageJ analyses to measure the percentage of area occupied by interstitial space in the renal cortex and medulla by thresholding the absence of H&E staining. Glomerular diameters were measured across 30 glomeruli per group of at least four animals using Imager s distance algorithm.

Immunofluorescence

Kidney sections were deparaffinized in xylene, rehydrated, and washed. After antigen retrieval, tissue sections were stained with fluorescein-labeled terminal deoxynucleotidyl transferase dUTP nick end labeling (TUNEL) kit (Roche, Mannheim, Germany). Slides were mounted using Vectashield Mounting Media containing DAPI (Vector Laboratories, Burlingame, Calif.). Tissue sections were imaged using the EVOS FL fluorescence microscope at 20× original magnification. TUNEL-positive cells from ten fields per kidney section and five sections per group of at least four animals were quantified using the ImageJ software's particle counter by thresholding for green fluorescence.

At the time of sacrifice, the CIS control group had undergone extensive kidney injury as evidenced by histologic examination with both H&E and PAS staining. In comparison to negative control and P2Ns-GA UA groups, the CIS control group showed greater interstitial expansion along with increased necrosis and atrophy of the tubules (see FIG. 3A).

Figures 3A, 3B, 3C, 3D:
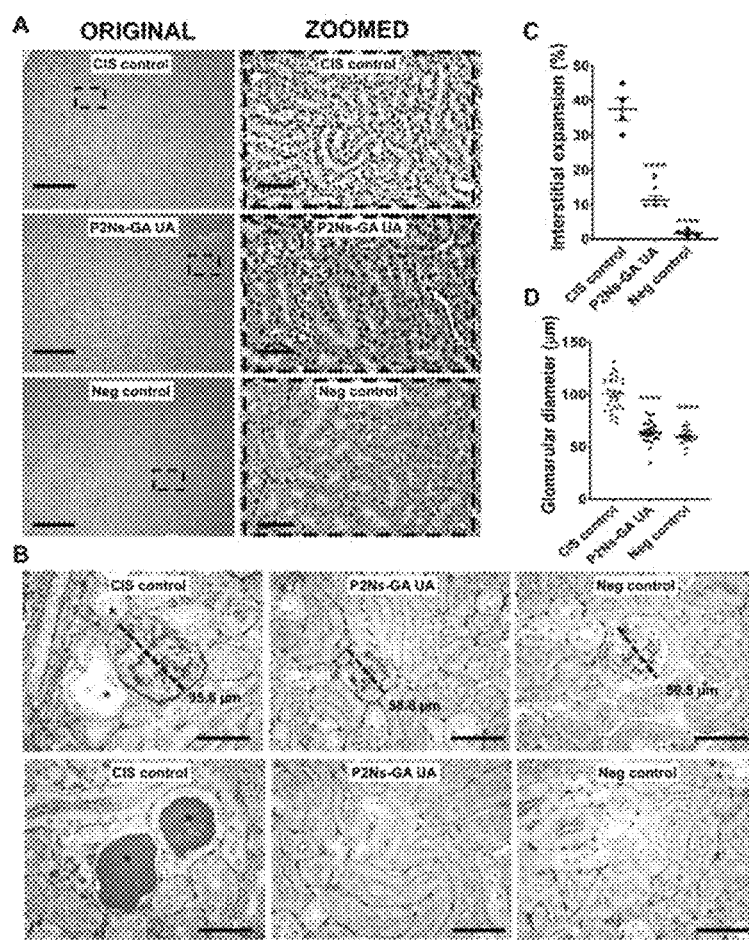
FIGS. 3A-3D show histopathological evaluation of kidney sections.

ImageJ analyses of H&E images indicated that the cortical and medullary area occupied by interstitial space was approximately 37% in the CIS control group, but only 11% and 2% for the P2Ns-GA UA and negative control groups, respectively (see FIG. 3C). At 40×, PAS staining further revealed tubular dilation, apoptotic bodies, prominent PAS-positive renal casts within tubular lumens, and thickening of glomerular basement membranes (see FIG. 3B). Cross-sectional glomerular diameter also increased in the CIS control group (see FIG. 3D), which suggested compensatory glomerular hypertrophy. In contrast, P2Ns-GA UA treatment significantly negated these morphological abnormalities.

Example 4

Protective Effects of Nanoparticle Compositions

The protective basis of UA was evaluated using the expression of a panel of microRNAs and mRNAs involved in the cytotoxic stress response. Small non-coding RNAs such as mature miRNAs have emerged as important biomarkers and mediators of renal injury. Two mature miRs were examined-miR-140-5p and miR-192-5p, which have been implicated in AKI.

Western Blot

Approximately 5 mg of kidney cortex from each mouse was homogenized in cold RIPA buffer. After centrifugation, the supernatant was collected and protein concentration was determined using the Bradford assay (Thermo Scientific, Waltham, Mass.). Approximately 30 μg of protein was subjected to denaturing SDS-PAGE. The gel-separated proteins were transferred to a 0.45 μm nitrocellulose membrane, followed by standard Western blot protocol.

Primary antibodies Nrf2 (CAT #MBS2538072, MyBiosource, San Diego, Calif.), P53 (CAT #928, Cell Signaling Technology, Danvers, Mass.), and GAPDH (CAT #2118, Cell Signaling Technology) were diluted at 1:1000, while Total OXPHOS Cocktail (CAT #ab110413, Abcam, Los Angeles, Calif.) was diluted at 1:250. HRP-conjugated secondary antibodies (Thermo Scientific): goat anti-mouse IgG and anti-rabbit igG were diluted at 1:5000. The ECL reagent was used to develop protein signals, and images were captured by the ChemiDoc imaging system (Bio-Rad, Hercules, Calif.).

RNA Isolation and PCR

Approximately 5 mg of kidney cortex was homogenized in Trizol solution. Micro RNA and large RNA were sequentially extracted and purified with E.Z.N.A. Micro RNA Kit (Omega Bio-tek, Norcross, Ga.) following manufacturer instructions. RNA concentrations were determined using the NanoQuant plate reader (Tecan Infinite M200). Reverse transcription for large RNA and miRNA were separately carried out using iScript gDNA Clear cDNA Synthesis Kit (Bio-Rad) and the miScript II RT Kit (Qiagen, Hilden, Germany), respectively. HiSpec Buffer was used in the latter RT reaction to target mature miRNA, and 1 μg of template RNA was used for all RT reactions. The CFX96 Touch Real-Time PCR Detection System (Bio-Rad) was used for qPCR. For gene expression, cDNA was amplified using appropriate primers (see Table 1), along with the iTaq Universal SYBR Green Supermix (Bio-Rad). Primers were pre-designed and validated by Harvard PGA Primerbank.

TABLE 1

List of primers used for quantitative PCR

| Gene | Forward Oligo | Reverse Oligo |
|---|---|---|
| Mt1 | 5'-AAGAGTGAGTTGGGACACCTT-3' | 5'-CGAGACAATACAATGGCCTCC-3' |
| Txnrd1 | 5'-CCCACTTGCCCCAACTGTT-3' | 5'-GGGAGTGTCTTGGAGGGAC-3' |
| Srxn1 | 5'-CCCAGGGTGGCGACTACTA-3' | 5'-GTGGACCTCACGAGCTTGG-3' |
| Cdkn1α/p21 | 5'-CCTGGTGATGTCCGACCTG-3' | 5'-CCATGAGCGCATCGCAATC-3' |
| Atf3 | 5'-GAGGATTTTGCTAACCTGACACC-3' | 5'-TTGACGGTAACTGACTCCAGC-3' |
| Trp53inp1 | 5'-AAGTGGTCCCAGAATGGAAGC-3' | 5'-GGCGAAAACTCTTGGGTTGT-3' |
| PARP1 | 5' -GGCAGCCTGATGTTGAGGT-3' | 5'-GCGTACTCCGCTAAAAAGTCAC-3' |
| PARG | 5'-AACGCCACCTCGTTTGTTTTC-3' | 5'-CACAGAACTCATCATGGAGTCA-3'A |
| Bcl-2 | 5'-ATGCCTTTGTGGAACTATATGGC-3' | 5'-GGTATGCACCCAGAGTGATGC-3' |
| Bax | 5'-TGAAGACAGGGGCCTTTTTG-3' | 5'-AATTCGCCGGAGACACTCG-3' |
| Ctnnb1 | 5'-ATGGAGCCGGACAGAAAAGC-3' | 5'-CTTGCCACTCAGGGAAGGA-3' |
| Tcf7 | 5'-AGCTTTCTCCACTCTACGAACA-3' | 5'-AGCTTTCTCCACTCTACGAACA-3' |
| Hif1α | 5'-ACCTTCATCGGAAACTCCAAAG-3' | 5'-ACTGTTAGGCTCAGGTGAACT-3' |
| Pgk1 | 5'-ATGTCGCTTTCCAACAAGCTG-3' | 5'-GCTCCATTGTCCAAGCAGAAT-3' |
| Actb | 5'-GGCTGTATTCCCCTCCATCG-3' | 5'-CCAGTTGGTAACAATGCCATGT-3' |

Mt1, metallothionein 1; Txnrd1, thioredoxin reductase 1; Srxn1, sulfiredoxin 1 homolog; Cdkn1α/p21, cyclin-dependent kinase inhibitor 1A/P21; Atf3, activating transcription factor 3; Trp53inp1, transformation-related protein 53-inducible nuclear protein 1; PARP1, poly (ADP-ribose) polymerase 1; PARG, poly(ADP-ribose) glycohydrolase; Ctnnb1, β-catenin; Tcf7, transcription factor 7, T cell specific; Hif1α, hypoxia-inducible factor-1α; Pgk1, phosphoglycerate kinase 1; Actb, β-actin.

For miRNA expression, cDNA was amplified using miScript Primer Assays for miR-192-5p and miR-140-5p (Qiagen), along with the miScript SYBR Green PCR Kit (Qiagen). ΔCt values were calculated with β-actin (gene expression) or RNU6 (miRNA) normalization, and fold change of the gene of interest between groups was expressed as $2^{-\Delta\Delta Ct}$.

Figures 4A, 4B:
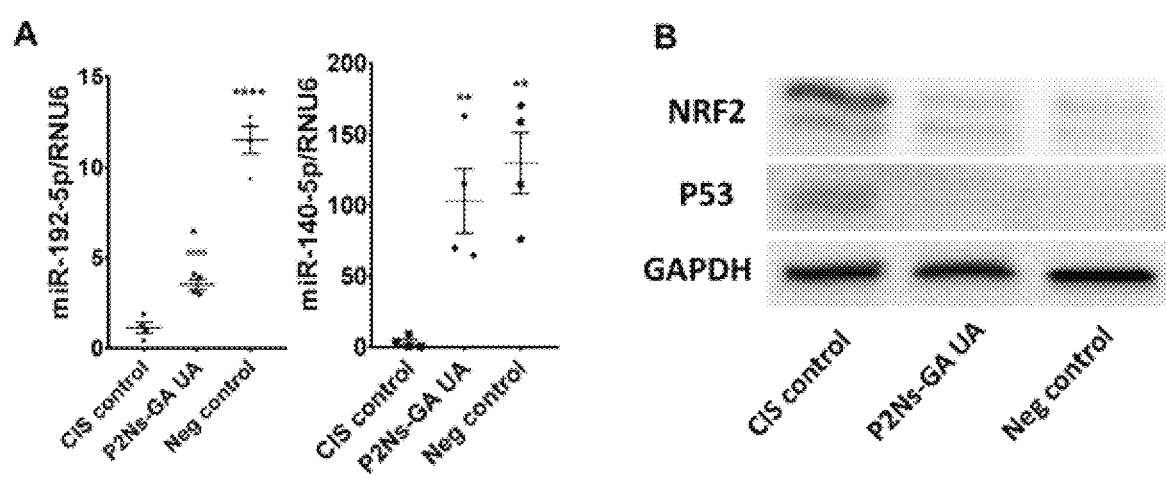
FIGS. 4A-4F show genetic targets of UA comprised of miRs and stress responsive genes. Renal cortex was homogenized following excision from mice. Real-time PCR and Western blots were carried out on Trizol RNA extracts and RIPA protein extracts, respectively.

Kidney-specific reductions in both miR-140-5p and miR-192-5p were observed in the CIS control group at sacrifice, whereas these changes were largely reversed with P2Ns-GA UA (see FIG. 4A).

Without being bound by any theory, it is believed that miR-140-5p and miR-192-5p associate with NRF2/ARE and P53 pathways, respectively. Oxidative stress, a key driver of CIS-induced renal injury, triggers the transcription of NRF2 and P53-inducible genes; the former encode primarily thiol antioxidants whereas the latter encode a variety of modulators of proliferation, DNA repair, and apoptosis.

Figures 4C, 4D:
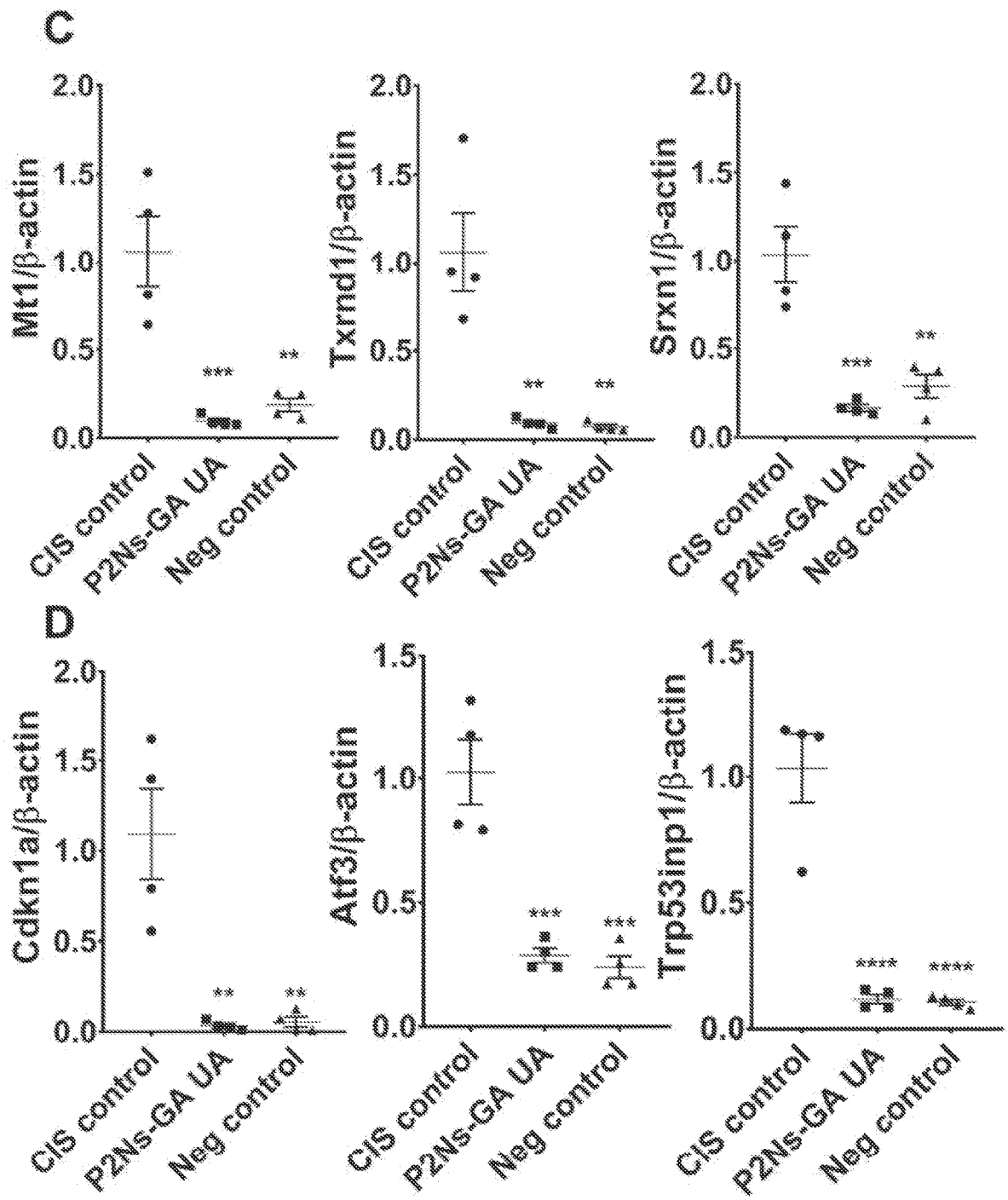

Renal expression of the NRF2 protein and NRF2-inducible genes: Mt1, Txnrd1, and Srxn1 was significantly higher in the CIS control group (8-12 fold, 7-14 fold, and 4-5 fold, respectively) compared to the P2Ns-GA UA and negative control groups (see FIGS. 4B-4C). Likewise, this pattern was observed with the P53 protein and P53-inducible genes: Cdkn1a (P21), Atf3, and Trp53inp1 (SIP), which in the CIS control group had increases of 7-49 fold, 3-4 fold, and 9-12 fold, respectively, compared with the P2Ns-GA UA and negative control groups (see FIGS. 4B and 4D). Because the CIS control group was terminally moribund, the renal overexpression of stress response genes likely reflected the severity of oxidative damage affecting this group, which cannot be overcome by endogenous protection mechanisms activated by NRF2, whereas P53 indicates activation of stress and apoptosis signaling.

Figures 4E, 4F:
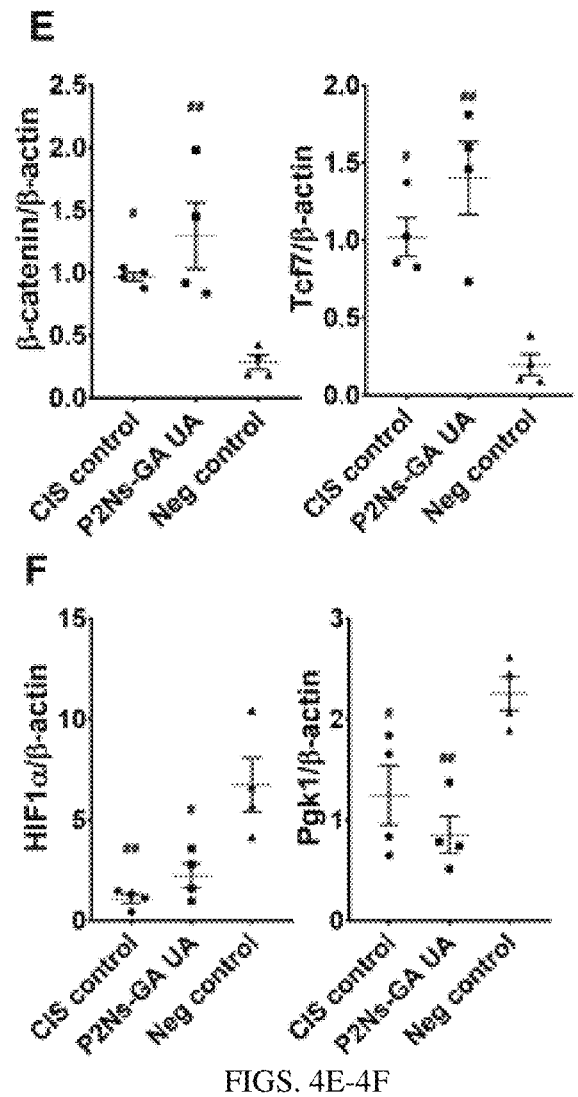

The Wnt/β-catenin pathway is involved in the regeneration of damaged renal parenchyma that accompanies CIS-induced AKI. Both the CIS control and P2Ns-GA UA groups exhibited similar increases in Wnt-signaling, as evidenced by the elevated expression of β-catenin and Tcf7, suggesting that the regulation of this pathway is independent of P2Ns-GA UA treatment (see FIG. 4E). On the other hand, activation of hypoxia-inducible genes have been shown to counteract CIS damage in both cancerous and normal cells, as well as promoting survival in ischemic/reperfusion AKI. However, P2Ns-GA UA did not alter the hypoxic state of the kidney, as both CIS control and P2Ns-GA UA groups had decreased expression of genes that are associated with hypoxia (see FIG. 4F).

Example 5

Downstream Effects of Renal Stress Response

Intracellular $NAD^+$ Measurement

Approximately 5 mg of kidney cortex from each mouse was homogenized in cold RIPA buffer. After centrifugation, approximately 50 μL of supernatant was processed in triplicate using Amplite Fluorimetric NAD Assay Kit (AAT Bioquest, Sunnyvale, Calif.) while following manufacturer instructions. Fluorescence at 420/480 nm was measured using the plate reader (Tecan Infinite M200) and NAD concentration determined using a standard curve constructed on the same day of the experiment. Protein concentration of the lysate was determined by the Bradford Assay (Bio-Rad) and served as normalization.

Depending on the magnitude of oxidative stress, subsequent P53 activation can lead to a cascade of cellular responses that include the attempted repair of DNA damage and if unsuccessful, cell death. The enzymes PARP1 and PARG, which catalyze polymerization and depolymerization of ADP-ribose onto their nuclear substrates, participate in both responses.

Figures 5A, 5B, 5C, 5D:
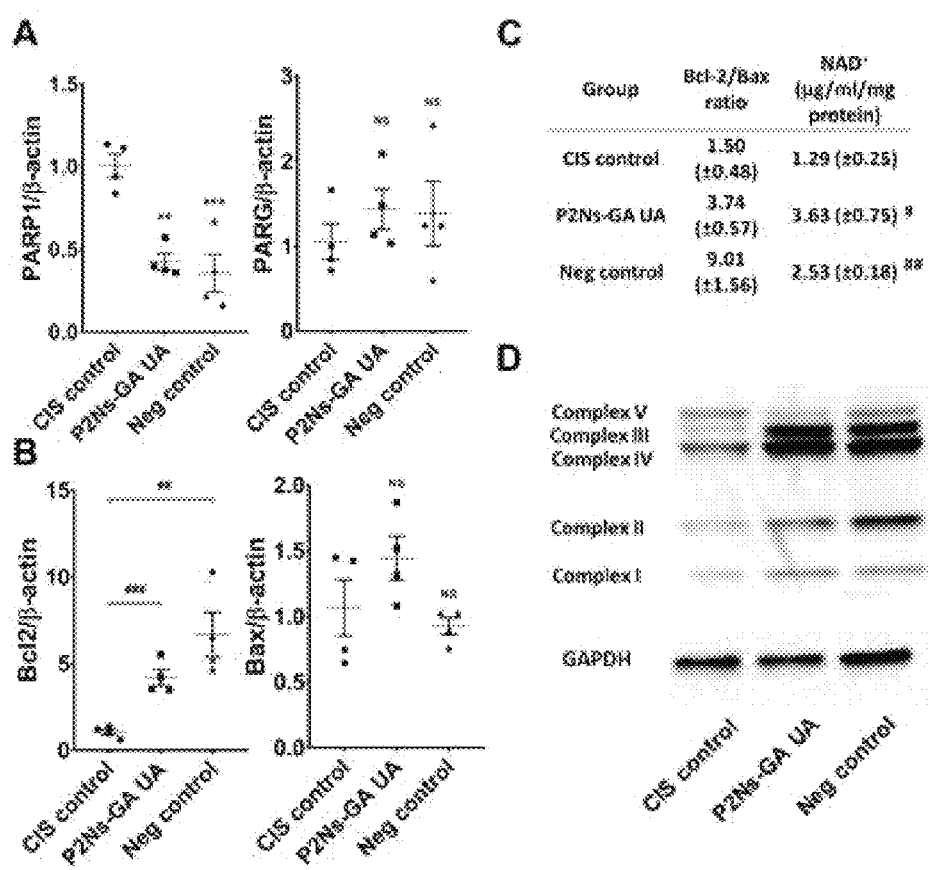
FIGS. 5A-5E show the downstream effects of oxidative stress and P53 activation includes PARP1 expression, apoptosis signaling, NAD depletion, and oxidative phosphorylation (OXPHOS) reduction.
Figure 5E:
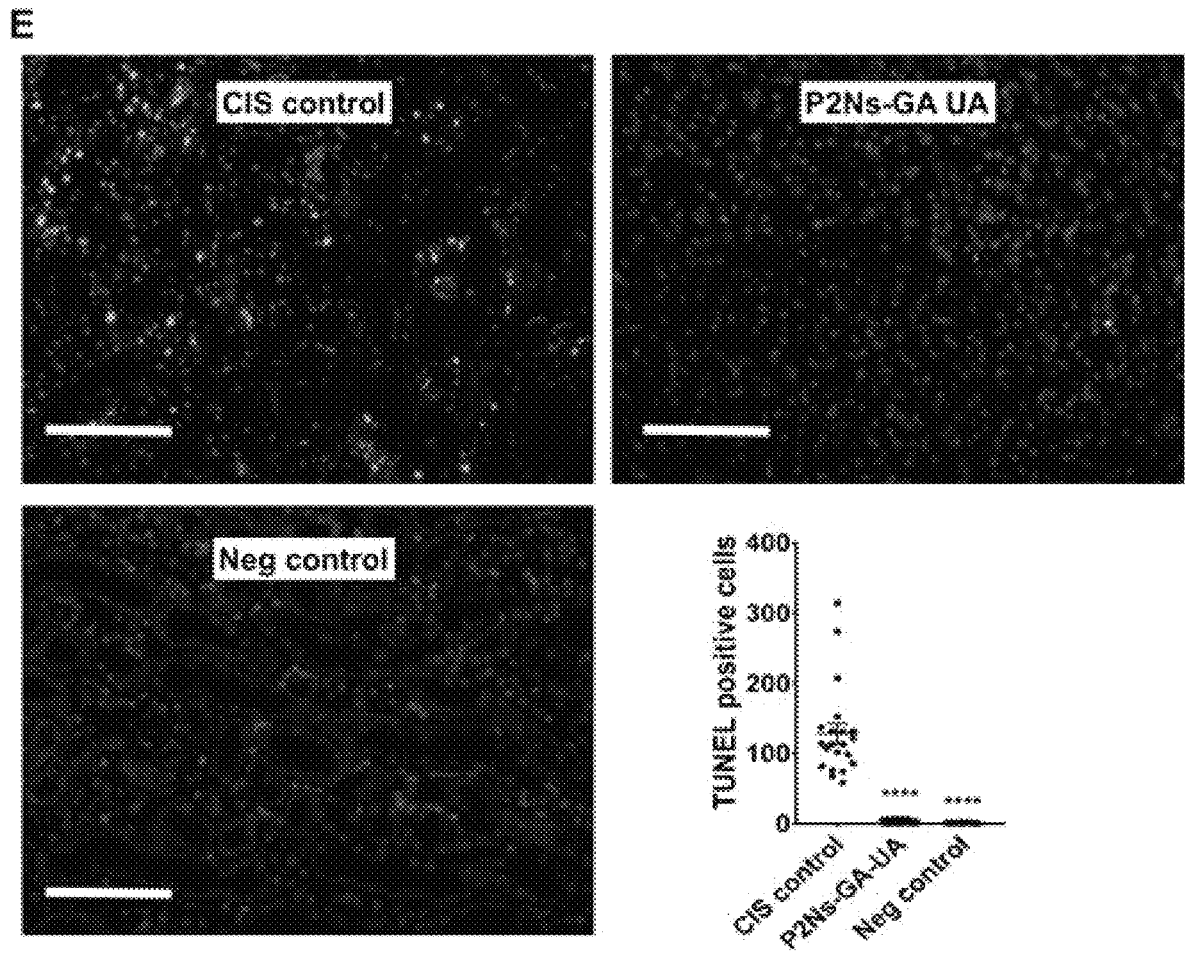

Although no change in the expression of PARG in any group was observed, elevated PARP1 expression was observed in the CIS control group (see FIG. 5A). Overexpression of PARP1 may itself act as both pro-apoptotic (via caspase-mediated cleavage) and necrotic (via depletion of NAD substrate) cell death signals. Indeed, reductions in both Bcl2/bax transcript ratio (an indicator of apoptosis), and intracellular NAD were observed in the CIS control group (see FIGS. 5B-5C). Additionally, CIS caused marked decreases in mitochondrial complexes I, II, III, and IV (see FIG. 5D). Finally, the CIS control kidney sections showed increased incidences of TUNEL positive cells—a sign of apoptosis-induced nuclear fragmentation (see FIG. 5E). In contrast, renal apoptosis as well as deficiencies in oxidative phosphorylation were less pronounced in the P2Ns-GA UA group.

Example 6

Administration of Nanoparticle Compositions to Dogs

Polymer Synthesis and Nanoparticle Preparation

For the instant example, polymers were first synthesized from pre-polymeric blocks of PEG and PLA; these were then crosslinked with cyclohexanetetracarboxylic dianhydride (HCDA) to provide periodically spaced carboxyl groups along the polymer backbone. An ethylene diamine linker was then added to the carboxyl group by 1-Ethyl-3-(3-dimethylaminopropyl)carbodiimide (EDC) chemistry, and GA was in turn conjugated to the linker. To obtain fluorescent polymers, NHS-fluorescein instead of GA was conjugated. GA-free polymers were likewise synthesized, consisting of all of the previous components except for GA and ethylene diamine Nanoparticle composition assembly utilized the oil-in-water emulsification method. UA-loaded nanoparticle compositions were prepared by adding polymers (with or without GA) and UA to water containing 1% (Di-n-dodecyl)-dimethylammonium bromide (DMAB). Fluorescent nanoparticles were prepared by adding a mixture of 5% fluorescein-conjugated polymers and 95% non-fluorescent polymers to water containing 1% DMAB. The nano-emulsions were collected by centrifugation, suspended in 5% sucrose, and lyophilized Immediately prior to use, water was added to the freeze-dried nanoparticles, attaining requisite concentrations.

Canine Pharmacokinetics

Eight healthy purpose-bred juvenile intact male beagles (Ridglan Farms, Mount Horeb, Wis.) were included in the instant example. All dogs were 4-6 months old throughout the study and were both single-housed and pair-housed in runs (2.1 m L×1.2 m W×3.0 m H). All the dogs used in the study provided controlled light cycle (day/night), temperature (21-22° C.), and humidity (55-60%) conditions. Water was available at all times and a maintenance diet was provided twice daily.

In total, 12 dogs were divided into three groups (n=4), each dog per group was administered a single oral dose, freeze-dried nanoparticle compositions suspended in water: Group 1 received P2Ns-GA-UA nanoparticle compositions (7.5 mg/kg); Group 2 received P2Ns-UA nanoparticle compositions (7.5 mg/kg); and Group 3 received plain UA (10 mg/kg) suspended in CMC. Blood was collected at 0.5 hours, 2 hours, 6 hours, 12 hours, 24 hours, and 48 hours. Plasma UA concentrations were determined using LC-MS. Detailed safety assessments of oral P2Ns-GA-UA and P2Ns-UA were evaluated pre- and 24-hours post dosing for clinical pathology tests such as complete blood count and serum biochemistry.

Figure 6:
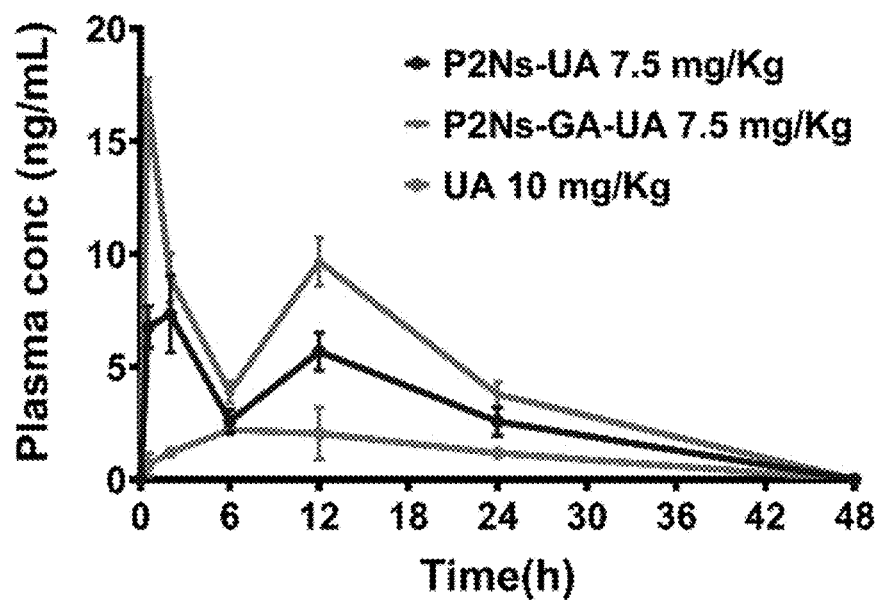
FIG. 6 shows the plasma UA concentrations observed for both nanoparticle compositions and for plain UA in dogs at 0.5-48 hours after the administration of a single oral dose. The table inset provides AUC (area under curve), T max (time to reach maximum concentration) and C max (maximum concentration) for the various groups.

Each dog was administered a single, 7.5 mg/kg dose (for P2Ns-GA-UA and P2Ns-UA) or 10 mg/kg dose (for UA) by feeding syringe, followed by multiple blood draws from the femoral vein at set intervals for up to 48 hours. Total serum UA concentration, which included both glucuronate and sulfate metabolites, was measured by LC-MS. After adjusting for dosage, administration of P2Ns-GA-UA nanoparticle compositions provided a 430% increase in area under curve (AUC) and 920% increase in maximum serum concentration (C max) when compared to UA. The advantage of P2Ns-GA-UA nanoparticle compositions compared to P2Ns-UA was also significant, albeit more moderate at 57% and 130% increase for AUC and C max, respectively (see FIG. 6).

Example 7

Combination Treatment with Nanoparticle Compositions and Cisplatin

The nanoparticle compositions of the present disclosure can be administered with an anti-cancer drug such as cisplatin to provide a synergistic effect in treating cancer cells. Co-administration of the nanoparticle compositions with cisplatin, or administering the two therapies at close to the same time, can improve the efficacy of cisplatin against cancer cells otherwise resistant against platinum-based anti-cancer drugs such as cisplatin.

Figure 7:
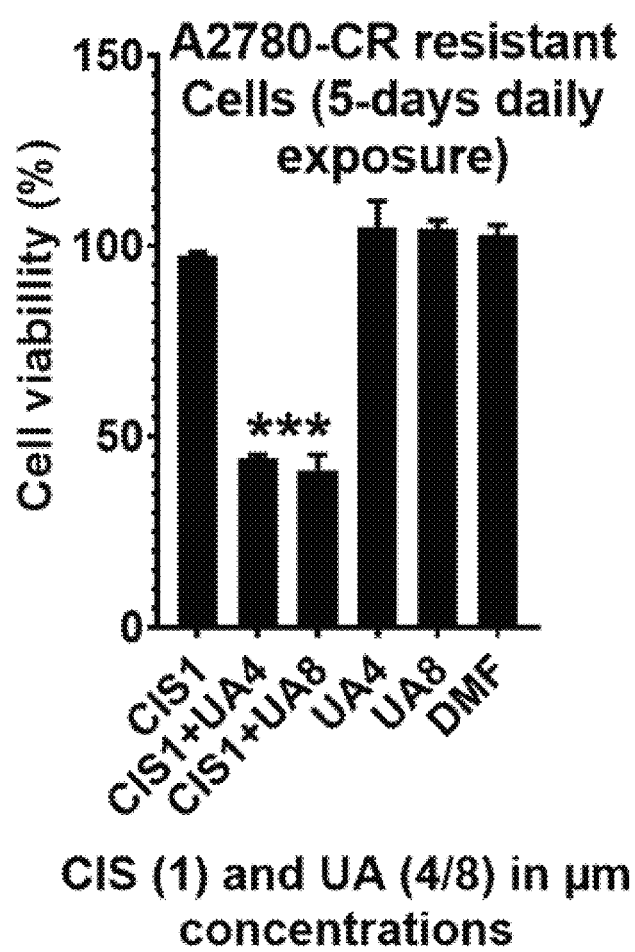
FIG. 7 shows that UA sensitizes cisplatin (CIS) to CIS-resistant A2780 ovarian cancer cells. A synergistic effect was observed using UA in combination with CIS, whereas UA and CIS administered alone at the same concentrations failed to cause cell death in the A2780 ovarian cancer cells.

Administration of the nanoparticle compositions and cisplatin can provide an unexpected synergistic effect to patients. As shown in FIG. 7, co-administration of the nanoparticle compositions and cisplatin provides a reduction in cell viability in cisplatin-resistant A2780 ovarian cancer cells compared to administration of each therapy individually (which failed to cause cell death).

For the instant example, 8-to-10 week old female athymic nude nu/nu mice can be injected i.p with about 1 million A2780CR cells suspended in ~200 microliters HBSS. After two weeks, the mice can be randomized into two groups. Cisplatin ("CIS"; Platinol-AQ) can be administered to the mice i.p at 10 mg/kg once a week over 8 weeks. The UA equivalent dose (50/75/100 mg/kg) of P2Ns-GA-UA nanoparticle compositions can be administered. For instance, the first dose can be administered at 30 minutes after cisplatin administration and can maintain 1- or 3-doses per week thereafter. The P2Ns-GA-UA nanoparticle compositions can be administered by oral gavage and administration can continue until each animal becomes moribund or completes 8 weeks of administration.

What is claimed is:

1. A method of treating a kidney injury in a patient in need thereof, said method comprising the step of administering a therapeutically effective amount of a nanoparticle composition to the patient, wherein the nanoparticle composition comprises i) a polymeric nanoparticle, ii) one or more ligands conjugated to the polymeric nanoparticle, and iii) urolithin A, and wherein the ligand is gambogic acid.

2. The method of claim 1, wherein the kidney injury is an acute kidney injury.

3. The method of claim 2, wherein the acute kidney injury is caused by a chemical selected from the group consisting of cisplatin, carboplatin, oxaliplatin, nedaplatin, or any combination thereof.

4. The method of claim 2, wherein the acute kidney injury is an ischemic/reperfusion acute kidney injury.

5. The method of claim 1, wherein the patient is an animal and wherein the animal is a human.

6. The method of claim 1, wherein the administration is an oral administration.

7. The method of claim 1, wherein the administration is a parenteral administration.

8. The method of claim 1, wherein method treats one or more symptoms of the kidney injury in the patient.

9. The method of claim 8, wherein the symptoms are selected from the group consisting of weight loss, kidney mass, kidney:body mass, serum creatinine concentration, serum BUN concentration, renal apoptosis, oxidative phosphorylation deficiencies, renal stress, and any combination thereof.

10. The method of claim 1, wherein the polymeric nanoparticle comprises a polymer/copolymer selected from the group consisting of polylactide, polycaprolactone, and combinations thereof.

* * * * *

SEQUENCE LISTING

<160> NUMBER OF SEQ ID NOS: 30

<210> SEQ ID NO 1
<211> LENGTH: 21
<212> TYPE: DNA
<213> ORGANISM: Artificial
<220> FEATURE:
<223> OTHER INFORMATION: Synthetic

<400> SEQUENCE: 1
aagagtgagt tgggacacct t                                                21

<210> SEQ ID NO 2
<211> LENGTH: 21
<212> TYPE: DNA
<213> ORGANISM: Artificial
<220> FEATURE:
<223> OTHER INFORMATION: Synthetic

<400> SEQUENCE: 2
cgagacaata caatggcctc c                                                21

<210> SEQ ID NO 3
<211> LENGTH: 19
<212> TYPE: DNA
<213> ORGANISM: Artificial
<220> FEATURE:
<223> OTHER INFORMATION: Synthetic

<400> SEQUENCE: 3
cccacttgcc ccaactgtt                                                   19

<210> SEQ ID NO 4
<211> LENGTH: 19
<212> TYPE: DNA
<213> ORGANISM: Artificial
<220> FEATURE:
<223> OTHER INFORMATION: Synthetic

<400> SEQUENCE: 4
gggagtgtct tggagggac                                                   19

```
<210> SEQ ID NO 5
<211> LENGTH: 19
<212> TYPE: DNA
<213> ORGANISM: Artificial
<220> FEATURE:
<223> OTHER INFORMATION: Synthetic

<400> SEQUENCE: 5
cccagggtgg cgactacta                                                  19

<210> SEQ ID NO 6
<211> LENGTH: 19
<212> TYPE: DNA
<213> ORGANISM: Artificial
<220> FEATURE:
<223> OTHER INFORMATION: Synthetic

<400> SEQUENCE: 6
gtggacctca cgagcttgg                                                  19

<210> SEQ ID NO 7
<211> LENGTH: 19
<212> TYPE: DNA
<213> ORGANISM: Artificial
<220> FEATURE:
<223> OTHER INFORMATION: Synthetic

<400> SEQUENCE: 7
cctggtgatg tccgacctg                                                  19

<210> SEQ ID NO 8
<211> LENGTH: 19
<212> TYPE: DNA
<213> ORGANISM: Artificial
<220> FEATURE:
<223> OTHER INFORMATION: Synthetic

<400> SEQUENCE: 8
ccatgagcgc atcgcaatc                                                  19

<210> SEQ ID NO 9
<211> LENGTH: 23
<212> TYPE: DNA
<213> ORGANISM: Artificial
<220> FEATURE:
<223> OTHER INFORMATION: Synthetic

<400> SEQUENCE: 9
gaggattttg ctaacctgac acc                                             23

<210> SEQ ID NO 10
<211> LENGTH: 21
<212> TYPE: DNA
<213> ORGANISM: Artificial
<220> FEATURE:
<223> OTHER INFORMATION: Synthetic

<400> SEQUENCE: 10
ttgacggtaa ctgactccag c                                               21

<210> SEQ ID NO 11
<211> LENGTH: 21
<212> TYPE: DNA
<213> ORGANISM: Artificial
<220> FEATURE:
<223> OTHER INFORMATION: Synthetic
```

<400> SEQUENCE: 11
aagtggtccc agaatggaag c                                          21

<210> SEQ ID NO 12
<211> LENGTH: 20
<212> TYPE: DNA
<213> ORGANISM: Artificial
<220> FEATURE:
<223> OTHER INFORMATION: Synthetic

<400> SEQUENCE: 12
ggcgaaaact cttgggttgt                                            20

<210> SEQ ID NO 13
<211> LENGTH: 19
<212> TYPE: DNA
<213> ORGANISM: Artificial
<220> FEATURE:
<223> OTHER INFORMATION: Synthetic

<400> SEQUENCE: 13
ggcagcctga tgttgaggt                                             19

<210> SEQ ID NO 14
<211> LENGTH: 22
<212> TYPE: DNA
<213> ORGANISM: Artificial
<220> FEATURE:
<223> OTHER INFORMATION: Synthetic

<400> SEQUENCE: 14
gcgtactccg ctaaaaagtc ac                                         22

<210> SEQ ID NO 15
<211> LENGTH: 21
<212> TYPE: DNA
<213> ORGANISM: Artificial
<220> FEATURE:
<223> OTHER INFORMATION: Synthetic

<400> SEQUENCE: 15
aacgccacct cgtttgtttt c                                          21

<210> SEQ ID NO 16
<211> LENGTH: 23
<212> TYPE: DNA
<213> ORGANISM: Artificial
<220> FEATURE:
<223> OTHER INFORMATION: Synthetic

<400> SEQUENCE: 16
cacagaactc atcatggagt caa                                        23

<210> SEQ ID NO 17
<211> LENGTH: 23
<212> TYPE: DNA
<213> ORGANISM: Artificial
<220> FEATURE:
<223> OTHER INFORMATION: Synthetic

<400> SEQUENCE: 17
atgcctttgt ggaactatat ggc                                        23

<210> SEQ ID NO 18

```
<211> LENGTH: 21
<212> TYPE: DNA
<213> ORGANISM: Artificial
<220> FEATURE:
<223> OTHER INFORMATION: Synthetic

<400> SEQUENCE: 18
ggtatgcacc cagagtgatg c                                              21

<210> SEQ ID NO 19
<211> LENGTH: 20
<212> TYPE: DNA
<213> ORGANISM: Artificial
<220> FEATURE:
<223> OTHER INFORMATION: Synthetic

<400> SEQUENCE: 19
tgaagacagg ggccttttg                                                 20

<210> SEQ ID NO 20
<211> LENGTH: 19
<212> TYPE: DNA
<213> ORGANISM: Artificial
<220> FEATURE:
<223> OTHER INFORMATION: Synthetic

<400> SEQUENCE: 20
aattcgccgg agacactcg                                                 19

<210> SEQ ID NO 21
<211> LENGTH: 20
<212> TYPE: DNA
<213> ORGANISM: Artificial
<220> FEATURE:
<223> OTHER INFORMATION: Synthetic

<400> SEQUENCE: 21
atggagccgg acagaaaagc                                                20

<210> SEQ ID NO 22
<211> LENGTH: 19
<212> TYPE: DNA
<213> ORGANISM: Artificial
<220> FEATURE:
<223> OTHER INFORMATION: Synthetic

<400> SEQUENCE: 22
cttgccactc agggaagga                                                 19

<210> SEQ ID NO 23
<211> LENGTH: 22
<212> TYPE: DNA
<213> ORGANISM: Artificial
<220> FEATURE:
<223> OTHER INFORMATION: Synthetic

<400> SEQUENCE: 23
agctttctcc actctacgaa ca                                             22

<210> SEQ ID NO 24
<211> LENGTH: 22
<212> TYPE: DNA
<213> ORGANISM: Artificial
<220> FEATURE:
<223> OTHER INFORMATION: Synthetic

<400> SEQUENCE: 24
```

```
agctttctcc actctacgaa ca                                             22

<210> SEQ ID NO 25
<211> LENGTH: 22
<212> TYPE: DNA
<213> ORGANISM: Artificial
<220> FEATURE:
<223> OTHER INFORMATION: Synthetic

<400> SEQUENCE: 25
accttcatcg gaaactccaa ag                                             22

<210> SEQ ID NO 26
<211> LENGTH: 21
<212> TYPE: DNA
<213> ORGANISM: Artificial
<220> FEATURE:
<223> OTHER INFORMATION: Synthetic

<400> SEQUENCE: 26
actgttaggc tcaggtgaac t                                              21

<210> SEQ ID NO 27
<211> LENGTH: 21
<212> TYPE: DNA
<213> ORGANISM: Artificial
<220> FEATURE:
<223> OTHER INFORMATION: Synthetic

<400> SEQUENCE: 27
atgtcgcttt ccaacaagct g                                              21

<210> SEQ ID NO 28
<211> LENGTH: 21
<212> TYPE: DNA
<213> ORGANISM: Artificial
<220> FEATURE:
<223> OTHER INFORMATION: Synthetic

<400> SEQUENCE: 28
gctccattgt ccaagcagaa t                                              21

<210> SEQ ID NO 29
<211> LENGTH: 20
<212> TYPE: DNA
<213> ORGANISM: Artificial
<220> FEATURE:
<223> OTHER INFORMATION: Synthetic

<400> SEQUENCE: 29
ggctgtattc ccctccatcg                                                20

<210> SEQ ID NO 30
<211> LENGTH: 22
<212> TYPE: DNA
<213> ORGANISM: Artificial
<220> FEATURE:
<223> OTHER INFORMATION: Synthetic

<400> SEQUENCE: 30
ccagttggta acaatgccat gt                                             22
```